United States Patent
Wilson et al.

(10) Patent No.: US 12,202,887 B2
(45) Date of Patent: *Jan. 21, 2025

(54) ERADICATION OF BACTERIAL BIOFILM USING ANTI-AMYLOID MONOCLONAL ANTIBODIES

(71) Applicants: Temple University-Of The Commonwealth System of Higher Education, Philadelphia, PA (US); LANKENAU INSTITUTE OF MEDICAL RESEARCH, Wynnewood, PA (US)

(72) Inventors: Cagla Tukel Wilson, Huntingdon Valley, PA (US); Scott Dessain, Wynnewood, PA (US)

(73) Assignees: Temple University-of The Commonwealth System of Higher Education, Philadelphia, PA (US); LANKENAU INSTITUTE OF MEDICAL RESEARCH, Wynnewood, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,952

(22) Filed: Jan. 20, 2022

(65) Prior Publication Data
US 2022/0227846 A1    Jul. 21, 2022

Related U.S. Application Data

(63) Continuation of application No. 17/058,575, filed as application No. PCT/US2019/033897 on May 24, 2019, now Pat. No. 11,897,942.

(60) Provisional application No. 62/676,390, filed on May 25, 2018.

(51) Int. Cl.
C07K 16/12    (2006.01)
A61P 31/04    (2006.01)

(52) U.S. Cl.
CPC .......... *C07K 16/1235* (2013.01); *A61P 31/04* (2018.01); *C07K 16/1228* (2013.01); *C07K 16/1232* (2013.01)

(58) Field of Classification Search
None
See application file for complete search history.

(56) References Cited

U.S. PATENT DOCUMENTS

2005/0112139 A1 *  5/2005  Karp ............... C07K 14/005
                                                    424/188.1

FOREIGN PATENT DOCUMENTS

| WO | WO-2005019270 A2 * | 3/2005 | |
|----|--------------------|--------|-----|
| WO | WO-2005049802 A2 * | 6/2005 | |
| WO | WO-2010045315 A1 * | 4/2010 | ............. C07K 14/65 |
| WO | WO-2010051502 A2 * | 5/2010 | ........... C07K 14/525 |
| WO | WO-2011162904 A2 * | 12/2011 | |
| WO | WO-2012096994 A2 * | 7/2012 | ......... C07K 16/1018 |
| WO | WO-2012158948 A1 * | 11/2012 | ............. A61P 31/12 |
| WO | WO-2013109185 A1 * | 7/2013 | |
| WO | WO-2015133882 A1 * | 9/2015 | |
| WO | WO-2016073963 A1 * | 5/2016 | |
| WO | WO-2017218707 A2 * | 12/2017 | |

OTHER PUBLICATIONS

Almagro et al. Frontiers in Bioscience 13:1619-1633, 2008.*
Edwards et al.(J. Mol. Biol. (2003) 334, 103-118.*

* cited by examiner

*Primary Examiner* — Oluwatosin A Ogunbiyi
(74) *Attorney, Agent, or Firm* — Riverside Law LLP

(57) ABSTRACT

The present invention features compositions comprising an anti-amyloid antibody and methods of treating microbial infection and treating or preventing microbial biofilms using the composition.

14 Claims, 22 Drawing Sheets
Specification includes a Sequence Listing.

48 hr STM 24 hr STM + 24 hr ALZ.3H3

ERADICATION OF BACTERIAL BIOFILM USING ANTI-AMYLOID MONOCLONAL ANTIBODIES

CROSS-REFERENCE TO RELATED APPLICATIONS

This application is a continuation of U.S. application Ser. No. 17/058,575, filed Nov. 24, 2020, which is a U.S. national phase application filed under 35 U.S.C. § 371 claiming benefit to International Patent Application No. PCT/US2019/033897, filed May 24, 2019, which is entitled to priority under 35 U.S.C. § 119 (e) to U.S. Provisional Application No. 62/676,390, filed May 25, 2018, each of which is hereby incorporated by reference herein in its entirety.

STATEMENT REGARDING FEDERALLY SPONSORED RESEARCH OR DEVELOPMENT

This invention was made with government support under AI132996 awarded by the National Institutes of Health (NIH). The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206455-0001-01US_Sequence_Listing_ST25.txt" in ASCII format. The text file containing the Sequence Listing of the present application was created on Jan. 12, 2022, and is 26,680 bytes in size.

BACKGROUND OF THE INVENTION

Bacterial biofilms are of significant relevance and are often deleterious in the medical setting. Shielded within a dense extracellular matrix, bacterial biofilms are highly resistant to antibiotics, antimicrobials and responses generated by innate immune cells (Thurlow et al., 2011, J Immunol, 186(11):6585-96). The treatment strategies to eradicate biofilms are limited. The current treatment strategy to eliminate biofilm associated infections is through the use of antibiotics. In comparison to planktonic bacteria, 100 to 1000 fold greater concentration of antibiotics is required to combat biofilm associated infections (Anwar and Costerton, 1990, Antimicrob Agents Chemother, 34(9):1666-71, Moskowitz et al., 2004, J Clin Microbiol, 42(5):1915-22). Within biofilms, bacteria are slow growing or persistent rendering most antibiotics that target cellular biology or bacterial replication ineffective (Keren et al., 2004, FEMS Microbiol Lett, 230(1):13-8, Brown et al., 1988, J Antimicrob Chemother, 22(6):777-80, Stewart, 2002, Int J Med Microbiol, 292(2):107-13, Lewis, 2001, Antimicrob Agents Chemother, 45(4):999-1007). As more than 65% of infections are due to bacterial biofilms (Larsen et al., 2007, Environ Microbiol, 9(12):3077-90, Costerton et al., 1999, Science, 284(5418):1318-22), novel treatments to disrupt bacterial biofilms is necessary. Disruption of the biofilm matrix would enhance the susceptibility of the biofilm to both innate immune system as well as antibiotic treatment thus promoting resolution of the biofilm.

A major proteinaceous component of enteric biofilms is amyloid curli. Amyloid curli is the most well characterized bacterial amyloid expressed within biofilms (Hung et al., 2013, MBio, 4(5):e00645-13). Curli is specifically expressed by bacteria of the Enterobacteriaceae family, although approximately 40% of bacterial species produce amyloids as a major component of biofilms (Larsen et al., 2007, Environ Microbiol, 9(12):3077-90). Defined by its hallmark beta sheet structure where the β-sheets are perpendicular to the fiber axis (Sunde et al., 1997, J Mol Biol, 273(3):729-39; Nelson et al., 2005, Nature, 435(7043):773-8; Sunde et al., 1997, Adv Protein Chem, 50:123-59), curli is expressed by the bidirectional curli specific gene csgBAC and csgDEFG operons (Chapman et al., 2002, Science, 295(5556):851-5). The production of curli is a highly regulated process. When grown under stressful conditions, activation of the csg genes leads the production of the main curli proteins (along with other accessory proteins), CsgA and CsgB (Chapman et al., 2002, Science, 295(5556):851-5; Zhou et al., 2012, Methods Mol Biol, 849:303-20). With the aid of other accessory proteins, CsgA is produced as a monomeric unit and is secreted extracellular where it fibrilizes into the mature curli amyloid fibril (Robinson et al., 2006, Mol Microbiol, 59(3):870-81). CsgB aids in the nucleation of CsgA monomers and attaches CsgA to the cell surface (White et al., 2001, J Mol Biol, 311(4):735-49; Hammer et al., 2007, Proc Natl Acad Sci USA., 104(30): 12494-9).

Curli has numerous functions within the enteric biofilm. Curli serves as a scaffold of which allows the formation of the mature three dimensional biofilm (Reisner et al., 2003, Mol Microbiol, 48(4):933-46; Costerton et al., 1995, Annu Rev Microbiol, 49:711-45). Forming a mesh like network, curli enshrouds the bacteria creating a protective capsule. Curli expressed by the single bacterium promotes adhesion of multiple bacteria within the biofilm as well as aiding in surface attachment (Kikuchi et al., 2005, Microbiol Immunol, 49(9):875-84). The production of other integral biofilm components of *S. Typhimurium*, such as cellulose, are dependent of the production of curli. Amyloids are highly resistant to proteolytic and chemical degradation. Amyloids such as curli need to be exposed 90 percent formic acid or hexafluoroisopropanol (HFIP) to depolymerize the fibril into monomeric subunits (Zhou et al., 2013, Methods Mol Biol, 966:53-75). Without the production of curli, biofilms of *S. Typhimurium* are destabilized and fail to form mature biofilms (Kikuchi et al., 2005, Microbiol Immunol, 49(9):875-84).

Bacterial biofilms are frequently associated with infections and are difficult to eradicate. Further, there is no treatment for clearing bacterial biofilms that form on indwelling medical device (catheters, heart valves, artificial joints, etc.), so that the foreign objects usually need to be removed and/or replaced, at great cost and morbidity to the patient. Biofilms are also important components of chronic bacterial wound infections.

Thus, there is a need in the art for methods for preventing biofilm formation as well as for disrupting formed biofilms for treatment and prevention of microbial infections. The current invention satisfies this unmet need.

SUMMARY OF THE INVENTION

In one embodiment, the invention relates to a composition comprising a therapeutic antibody wherein the antibody is specific for binding to an epitope of curli and further wherein the epitope of curli comprises a sequence having homology to an antibody binding site of one or more heterologous amyloid proteins.

In one embodiment, the antibody inhibits fibrillization of one or more heterologous amyloid proteins. In embodiment, the antibody inhibits fibrillization of amyloid-β.

In one embodiment, the antibody prevents biofilm formation or alters biofilm architecture. In one embodiment, the antibody is effective in reducing biofilm mass. In one embodiment, the biofilm mass is associated with a gram-positive bacteria, a gram-negative bacteria, or a combination thereof.

In one embodiment, the antibody is ALZ.3H3, ALZ.2C10, ALZ.4G1, or ALZ.4A6.

In one embodiment, the antibody inhibits amyloid-β fibrillization and prevents biofilm formation or alters biofilm architecture. In one embodiment, the antibody is an ALZ.3H3 antibody. In one embodiment the ALZ.3H3 antibody comprises at least one of a heavy chain amino acid sequence as set forth in SEQ ID NO:2 and a light chain amino acid sequence as set forth in SEQ ID NO:35. In one embodiment the ALZ.3H3 antibody comprises at least one of a heavy chain amino acid sequence encoded by a nucleotide sequence as set forth in SEQ ID NO:1 and a light chain amino acid sequence encoded by a nucleotide sequence as set forth in SEQ ID NO:34.

In one embodiment, the antibody prevents biofilm formation or alters biofilm architecture. In one embodiment, the antibody is an ALZ.4G1 antibody. In one embodiment the ALZ.4G1 antibody comprises at least one of a heavy chain amino acid sequence as set forth in SEQ ID NO:61 and a light chain amino acid sequence as set forth in SEQ ID NO:63. In one embodiment the ALZ.4G1 antibody comprises at least one of a heavy chain amino acid sequence encoded by a nucleotide sequence as set forth in SEQ ID NO:60 and a light chain amino acid sequence encoded by a nucleotide sequence as set forth in SEQ ID NO:62.

In one embodiment, the antibody inhibits amyloid-β fibrillization. In one embodiment, the antibody is an ALZ.4A6 antibody. In one embodiment the ALZ.4A6 antibody comprises at least one of a heavy chain amino acid sequence as set forth in SEQ ID NO:57 and a light chain amino acid sequence as set forth in SEQ ID NO:59. In one embodiment the ALZ.4A6 antibody comprises at least one of a heavy chain amino acid sequence encoded by a nucleotide sequence as set forth in SEQ ID NO:56 and a light chain amino acid sequence encoded by a nucleotide sequence as set forth in SEQ ID NO:58

In one embodiment, the composition is for application to a surface of a medical device.

In one embodiment, the composition comprises an antibiotic.

In one embodiment, the composition comprises one or more pharmaceutically acceptable carriers or excipients.

In one embodiment, the formulation is a topical formulation in the form of a cream, a lotion, an ointment, a hydrogel, a colloid, a gel, a foam, an oil, a milk, a suspension, a wipe, a sponge, a solution, an emulsion, a paste, a patch, a pledget, a swab, a dressing, a spray or a pad.

In one embodiment, the invention relates to a method of decolonizing a microbial organism comprising contacting the microbial organism with a composition comprising a therapeutic antibody, wherein the antibody is specific for binding to an epitope of curli and further wherein the epitope of curli comprises a sequence having homology to an antibody binding site of one or more heterologous amyloid proteins. In one embodiment, the antibody the antibody inhibits fibrillization of one or more heterologous amyloid proteins, prevents biofilm formation, alters biofilm architecture, or any combination thereof. In one embodiment, the antibody is ALZ.3H3, ALZ.4G1, ALZ.2C10 or ALZ.4A6.

In one embodiment, the antibody inhibits amyloid-β fibrillization and prevents biofilm formation or alters biofilm architecture. In one embodiment, the antibody is an ALZ.3H3 antibody. In one embodiment the ALZ.3H3 antibody comprises at least one of a heavy chain amino acid sequence as set forth in SEQ ID NO:2 and a light chain amino acid sequence as set forth in SEQ ID NO:35. In one embodiment the ALZ.3H3 antibody comprises at least one of a heavy chain amino acid sequence encoded by a nucleotide sequence as set forth in SEQ ID NO:1 and a light chain amino acid sequence encoded by a nucleotide sequence as set forth in SEQ ID NO:34.

In one embodiment, the antibody prevents biofilm formation or alters biofilm architecture. In one embodiment, the antibody is an ALZ.4G1 antibody. In one embodiment the ALZ.4G1 antibody comprises at least one of a heavy chain amino acid sequence as set forth in SEQ ID NO:61 and a light chain amino acid sequence as set forth in SEQ ID NO:63. In one embodiment the ALZ.4G1 antibody comprises at least one of a heavy chain amino acid sequence encoded by a nucleotide sequence as set forth in SEQ ID NO:60 and a light chain amino acid sequence encoded by a nucleotide sequence as set forth in SEQ ID NO:62.

In one embodiment, the antibody inhibits amyloid-β fibrillization. In one embodiment, the antibody is an ALZ.4A6 antibody. In one embodiment the ALZ.4A6 antibody comprises at least one of a heavy chain amino acid sequence as set forth in SEQ ID NO:57 and a light chain amino acid sequence as set forth in SEQ ID NO:59. In one embodiment the ALZ.4A6 antibody comprises at least one of a heavy chain amino acid sequence encoded by a nucleotide sequence as set forth in SEQ ID NO:56 and a light chain amino acid sequence encoded by a nucleotide sequence as set forth in SEQ ID NO:58.

In one embodiment, the invention relates to a method of destroying or disrupting or inhibiting or reducing biofilm formation of a microbial organism comprising contacting the microbial organism with a composition comprising a therapeutic antibody, wherein the antibody is specific for binding to an epitope of curli and further wherein the epitope of curli comprises a sequence having homology to an antibody binding site of one or more heterologous amyloid proteins. In one embodiment, the antibody the antibody inhibits fibrillization of one or more heterologous amyloid proteins, prevents biofilm formation, alters biofilm architecture, or any combination thereof. In one embodiment, the microbial organism is a bacterium.

In one embodiment, the invention relates to a method of treating a microbial infection in a subject comprising administering to the subject a therapeutically effective amount of a composition comprising a therapeutic antibody, wherein the antibody is specific for binding to an epitope of curli and further wherein the epitope of curli comprises a sequence having homology to an antibody binding site of one or more heterologous amyloid proteins. In one embodiment, the antibody the antibody inhibits fibrillization of one or more heterologous amyloid proteins, prevents biofilm formation, alters biofilm architecture, or any combination thereof. In one embodiment, the antibody is ALZ.3H3, ALZ.4G1, ALZ.2C10 or ALZ.4A6.

In one embodiment, the microbial infection is a bacterial infection. In one embodiment, the bacterial infection is characterized by colonization of a bacterium. In one embodiment, the bacterial infection is characterized by biofilm formation.

In one embodiment, the microbial infection is a topical infection. In one embodiment, the topical infection is a wound, ulcer or lesion.

BRIEF DESCRIPTION OF THE DRAWINGS

FIG. 1A depicts exemplary experimental results demonstrating that the architecture of *S. Typhimurium* biofilm is altered with different treatments. FIG. 1B depicts exemplary images used to quantify the particles in the biofilm. FIG. 1C depicts an exemplary graph demonstrating the numbers of particles in the disperse portion of the biofilms (greater than 20 μM from the surface) in FIG. 1A.

FIG. 2A depicts a schematic demonstrating the experimental design. FIG. 2B depicts exemplary experimental results demonstrating the *S. Typhimurium* biofilm architecture with each treatment. FIG. 2C depicts an exemplary graph demonstrating the numbers of particles in the disperse portion of the biofilms (greater than 20 μM from the surface) in FIG. 2B.

FIG. 4A depicts a confocal analysis of biofilms of *S. Typhimurium* grown in the presence (10 ug/ml, 25 ug/ml, 50 ug/ml, 250 ug/ml, 500 ug/ml) or absence (untreated) of 3H3. Biofilms were stained with syto9 (green nucleic acid stain for bacteria) and amyloid dye Congo red (red curli). Biofilms imaged using Leica TCS confocal at 63×. Biofilm 3D reconstructions created using ImageJ 3D viewer software. Scale bar represents 50 um. FIG. 4B depicts the biofilm thickness (um) of biofilms of *S. Typhimurium* grown in the presence (10 ug/ml, 25 ug/ml, 50 ug/ml, 250 ug/ml, 500 ug/ml) or absence (untreated) of 3H3. Thickness measured using Leica TCS confocal microscopy software.

FIG. 5A depicts exemplary experimental results demonstrating that pan-amyloid antibodies prevent fibrillization in a Thioflavin T assay. FIG. 5A depicts exemplary experimental results demonstrating the lag time required for monomers to self-associate in the presence of pan-amyloid antibodies.

DETAILED DESCRIPTION

Figure 1A:
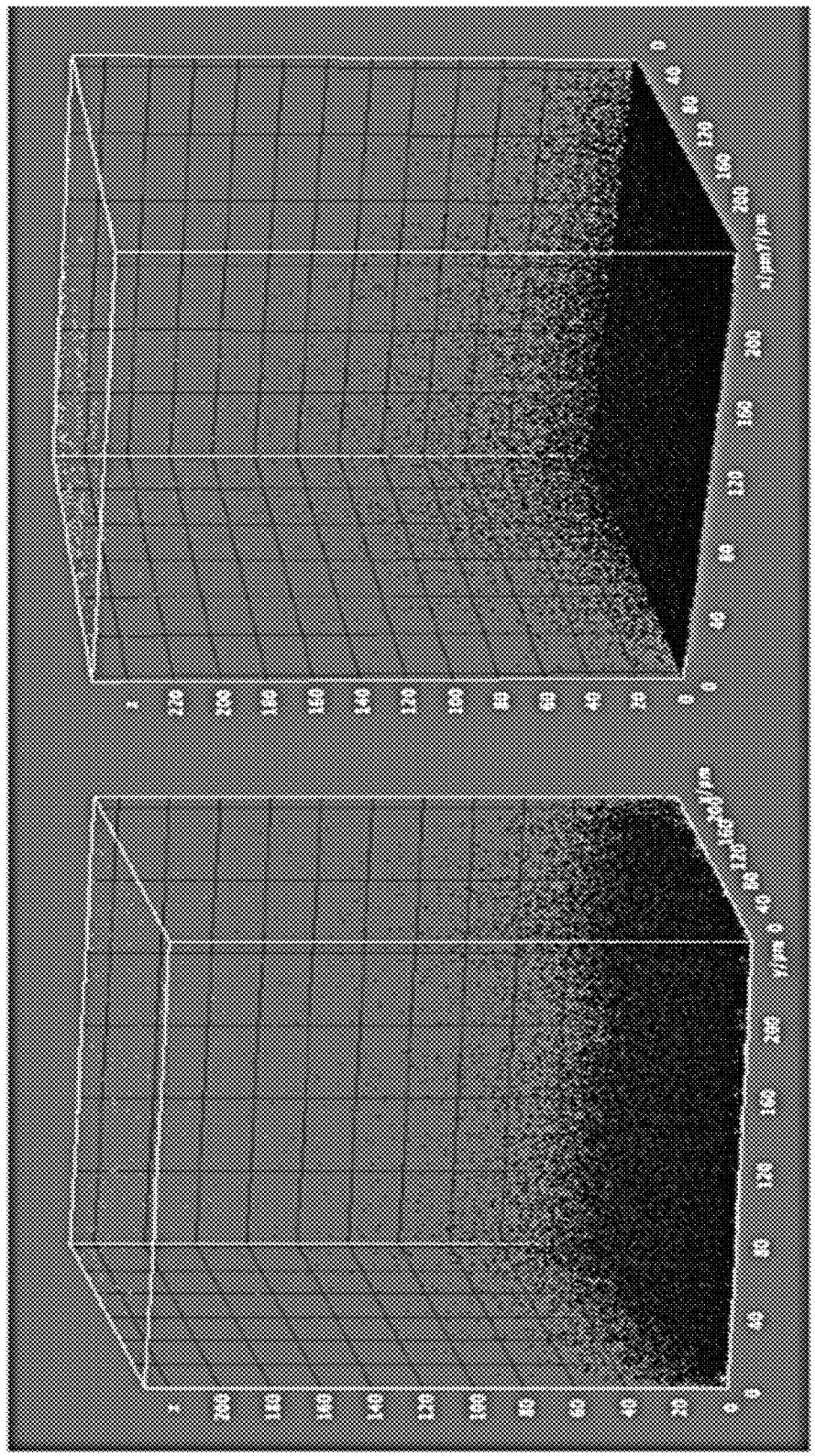
FIG. 1A through FIG. 1C depict exemplary experimental results demonstrating that the monoclonal antibody ALZ.3H3 disrupts *S. Typhimurium* biofilm architecture and integrity.
Figure 1A:
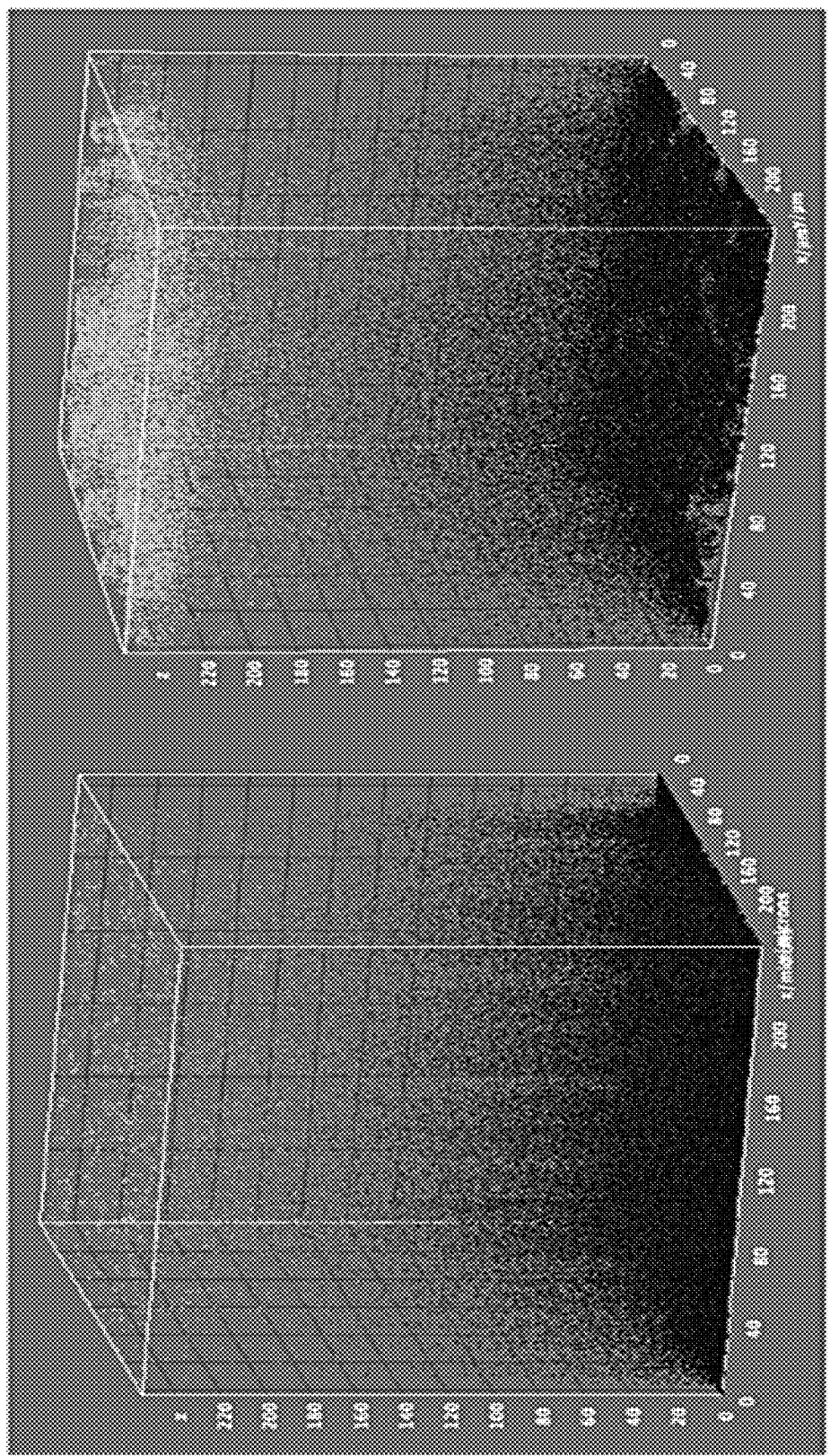

The present invention is based, in part, on the discovery that antibodies having pan-amyloid binding activity have the ability to inhibit biofilm formation by preventing amyloid fibrillization. Therefore, the invention provides compositions and methods to prevent biofilm formation by targeting the amyloid component of biofilms using pan-amyloid antibodies. In one embodiment, the invention provides compositions and methods of using an anti-amyloid monoclonal antibody that targets biofilm by way of targeting curli. In one aspect, the invention relates to the use of an anti-amyloid antibody wherein the antibody is specific for an amyloid beta sheet structure. In one embodiment, the antibody is ALZ.3H3 or ALZ.4G1.

In one embodiment, the invention provides compositions and methods to target a novel antigen such as curli and thereby change the paradigm for treating deep-seated and foreign-body/biofilm-associated infections. In one embodiment, the invention provides improvements to the treatment of multi-drug resistant bacteria by targeting an antigen that is non-cross resistant with existing drug resistance phenotypes.

In one embodiment, the invention provides a novel therapeutic target that allows the treatment of biofilm-producing bacteria using a human monoclonal antibody that can combat a diversity of gram positive and gram negative bacterial biofilms. In one embodiment, the antibody can remove a biofilm from an indwelling medical device.

In one embodiment, the invention relates to a method of treating a subject infected with a microbial species, the method comprising administering to the subject at least one antibody, wherein the at least one antibody specifically binds to an amyloid beta sheet structure.

In one embodiment, the method further comprises the administration of an antibiotic. In one embodiment, the antibody of the invention (e.g., anti-amyloid monoclonal antibody) and be combined with antibiotics to reduce the biofilm mass by targeting curli.

In another aspect, the invention relates to a method of treating, reducing, or preventing biofilm formation, wherein the composition comprises at least one antibody, wherein the at least one antibody specifically binds to an amyloid beta sheet structure. In one embodiment, the method further comprises the administration of an antibiotic.

In one embodiment, the invention provides methods of coating the surface of a medical device (e.g., catheter) with a composition of the invention to reduce biofilm mass.

In one embodiment, the invention also provides the use of the compositions of the invention in combination with agents (such as DNase) that target other components of the extracellular matrix. In one embodiment, the compositions of the invention can be used to treat biofilm matrix associated with excess DNA such as *Pseudomonas aeruginasa* biofilms.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

For purposes of interpreting this specification, the following definitions will apply and whenever appropriate, terms used in the singular will also include the plural and vice versa.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "analog" or "functional analog" refers to a related modified form of a polypeptide, wherein at least one amino acid substitution, deletion, or addition has been made such that said analog retains substantially the same biological activity as the unmodified form, in vivo and/or in vitro.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present invention are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

The term "agent" includes any substance, metabolite, molecule, element, compound, or a combination thereof. It includes, but is not limited to, e.g., protein, oligopeptide, small organic molecule, glycan, polysaccharide, polynucleotide, and the like. It can be a natural product, a synthetic compound, a chemical compound, or a combination of two or more substances. Unless otherwise specified, the terms "agent," "substance," and "compound" can be used interchangeably. Further, a "test agent" or "candidate agent" is generally a subject agent for use in an assay of the invention.

The term "binding" refers to a direct association between at least two molecules, due to, for example, covalent, electrostatic, hydrophobic, ionic and/or hydrogen-bond interactions.

As used herein, the term "biofilm" refers to matrix-enclosed microbial accretions to biological or non-biological surfaces in which microorganisms are dispersed and/or form colonies. The biofilm typically is made of polysaccharides and other macromolecules. Biofilm formation represents a protected mode of growth that allows cells to survive in hostile environments.

As used herein, the term "biofilm formation" is intended to include the formation, growth, and modification of the microbial colonies contained with biofilm structures, as well as the synthesis and maintenance of a polysaccharide matrix of the biofilm structures. Also within the scope of this term is formation of protein-based biofilms that do not secrete polysaccharide in the matrix but which comprise proteins that permit bacteria to form biofilm architecture.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

A "chimeric antibody" refers to a type of engineered antibody which contains a naturally-occurring variable region (light chain and heavy chains) derived from a donor antibody in association with light and heavy chain constant regions derived from an acceptor antibody.

"Contacting" refers to a process in which two or more molecules or two or more components of the same molecule or different molecules are brought into physical proximity such that they are able undergo an interaction. The term "contacting" includes, but is not limited to, impregnating, compounding, mixing, integrating, coating, rubbing, painting, spraying, immersing, rolling, smearing and dipping.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap temporally with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared multiplied by 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

As used herein, the term "microbial organism" or "microbe," or "microbial," or "microorganism" refers to a domain (Bacteria) of prokaryotic round, spiral, or rod-shaped single-celled, multi-celled, or acelled microorganisms that may lack cell walls or are Gram-positive or Gram-negative or alteration thereof (i.e. *Mycobacterium*) if they have cell walls, that are often aggregated into colonies or motile by means of flagella, that typically live in soil, water, organic matter, or the bodies of plants and animals, that are usually autotrophic, saprophytic, or parasitic in nutrition, and that are noted for their biochemical effects and pathogenicity. The term is intended to encompass prokaryotic or eukaryotic cells or organisms having a microscopic size and includes bacteria, viruses, archaea and eubacteria of all species as well as eukaryotic microorganisms such as yeast and fungi. The term also includes cell cultures of any species that can be cultured for the production of a biochemical. In one non-limiting example, the activity of a microbial organism can be measured by calculating the log reduction in number of the microorganism.

As used herein, the term "microbial colonization" refers to the formation of compact population groups of the same type of microorganism, such as the colonies that develop when a microbial cell begins reproducing. The microbial colonization may or may not cause disease symptoms. Decolonization refers to a reduction in the number of microbial organisms present. When the microbial organisms are completely decolonized, the microbial organisms have been eradicated and are non-detectable.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

"Parenteral" administration of an immunogenic composition includes, e.g., subcutaneous (s.c.), intravenous (i.v.), intramuscular (i.m.), or intradermal (i.d.) injection, or infusion techniques.

The terms "patient," "subject," "individual," and the like are used interchangeably herein, and refer to any animal, or cells thereof, whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "X," the presence of a molecule containing epitope X (or free, unlabeled A), in a reaction containing labeled "X" and the antibody, will reduce the amount of labeled X bound to the antibody.

The term "therapeutic" as used herein means a treatment and/or prophylaxis. A therapeutic effect is obtained by suppression, diminution, remission, or eradication of a disease state.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces bacterial infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. The term "treating" or "treatment" also refers to a reduction in the severity of one or more symptoms by about 10%, about 20%, about 30%, about 40%, about 50%, about 60%, about 70%, about 80%, about 90% or about 100%.

As used herein, the term "topical administration" refers to the delivery to a subject by contacting the formulation directly to a surface or localized region of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition.

As used herein, the term "topical formulation" (synonymously, "topical composition") is used herein to refer to a pharmaceutical preparation intended for topical or local application to an afflicted region of a subject in need thereof, and includes such dosage forms as gel, cream, ointment, emulsion, suspension, solution, drops, lotion, paint, pessary, douche, suppository, troche, spray, sponge, film, or foam. Preferably, the topical formulation is in the form of a cream, a gel, or an ointment.

"Variant" of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based, in part, on the identification of a novel therapeutic target that allows the treatment of biofilm-producing bacteria using a human monoclonal antibody which can combat a diversity of gram positive and gram negative bacterial biofilms, and even remove a biofilm from an indwelling medical device. This invention enables novel mAb drugs that target a novel antigen and will (1) change the paradigm for treating deep-seated and foreign-body/biofilm-associated infections, (2) improve treatment of multi-drug resistant bacteria by targeting an antigen that is non-cross resistant with existing drug resistance phenotypes, and (3) be effective against a wide variety of bacteria.

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. Described herein is the surprising and unexpected discovery that antibodies having pan-amyloid binding activity disrupt biofilms from multiple microbial species. Further, a combination of an anti-amyloid antibody of the invention and an antibiotic treatment, when used to treat a microbial organism, demonstrates synergistic effect against a microbial, colonization or infection or biofilm formation. As used herein, the term "synergistic" refers to the effect obtained by combining compounds and/or agents that is greater than the effect obtained by the separate addition of each compound. The combination treatment of the present invention has shown a synergistic effect as measured by, for example, the extent of the response, the duration of response, the response rate, the stabilization rate, the duration of stabilization, the time to reduce or clear the infections, the time to eradicate the microorganisms, to that achievable on dosing one or other of the components of the combination treatment at its conventional dose. For example, the effect of the combination treatment of the present invention is synergistic because the combination treatment is therapeutically superior to the effect achievable with one component alone or the additive effect of the combination components acting separately. The superior effect can be improved reduction in drug resistance from the microbial organisms, the extent to which the microbial organisms are eradicated and become non-detectable by the combination treatment. Also for example, the effect of the combination treatment of the present invention is synergistic because it takes shorter time to kill the microorganisms and clear the infections. Also for example, the effect of the combination treatment of the present invention is synergistic because the combination treatment offers broader spectrum of antimicrobial activities than those with one component alone. Also for example, the effect of the combination treatment of the present invention is synergistic because one of the components in the composition described in this invention is dosed at its conventional dose and the other component(s) is/are dosed at a reduced dose and the therapeutic effect, as measured by, for example, the extent of the killing and/or inhibiting growth of the microorganisms such as bacteria, the time to kill and/or inhibit growth of the microorganisms such as bacteria, or the time to destroy or inhibit microbial colonies, or the time to disrupt or inhibit or reduce biofilm formation or growth, is equivalent to that achievable on dosing conventional amounts of the components of the combination treatment.

Compositions

The composition of the invention can treat, prevent and/or protect against any disease, disorder, or condition associated with a bacterial activity. In certain embodiments, the composition can treat, prevent, and or/protect against bacterial infection. In certain embodiments, the composition can treat, prevent, and or/protect against bacterial biofilm formation. In certain embodiments, the invention provides a novel therapeutic target that allows the treatment of biofilm-producing bacteria using a human monoclonal antibody that can combat a diversity of gram positive and gram negative bacterial biofilms.

In certain embodiments, the composition can treat, prevent, and or/protect against Enterobacteriaceae, Bacteroidetes, Proteobacteria, Firmicutes or Thermodesulfobacteria infection. In certain embodiments, the composition can treat, prevent, and or/protect against Enterobacteriaceae, Bacteroidetes, Proteobacteria, Firmicutes or Thermodesulfobacteria biofilm formation. In certain embodiments, the composition can treat, prevent, and or/protect against *Salmonella typhimurium* (*S Typhimurium*) infection. In certain embodiments, the composition can treat, prevent, and or/protect against *S Typhimurium* biofilm formation. In certain embodiments, the composition can treat, prevent, and or/protect against *Escherichia coli* (*E. coli*) infection. In certain embodiments, the composition can treat, prevent, and or/protect against *E. coli* biofilm formation. In certain embodiments, the composition can treat, prevent, and or/protect against *Yersinia pestis* (*Y. pestis*) infection. In certain embodiments, the composition can treat, prevent, and or/protect against *Y. pestis* biofilm formation. In certain embodiments, the composition can treat, prevent, and or/protect against a disease including, but not limited to, meningitis, enteritis, plague, and sepsis.

In various embodiments, the present invention includes amyloid inhibitor compositions. In various embodiments, the amyloid inhibitor compositions of the invention diminish or inhibit amyloid fibrillization. In one embodiment, the amyloid inhibitor targets the major constituent of enteric biofilms, amyloid curli. In one embodiment, the invention provides an amyloid inhibitor that targets curli within biofilms that results in alterations in biofilm architecture, stability and overall result in reduction of the biofilm.

In one embodiment, the invention provides amyloid inhibitors that bind to and inhibit the fibrillization of bacterial amyloid curli implicated in biofilm formation. In one embodiment, the amyloid inhibitors are human monoclonal antibodies that exhibit reactivity against amyloid-β as well exhibit anti-curli properties within the context of bacterial biofilms.

It will be understood by one skilled in the art, based upon the disclosure provided herein, that a decrease in amyloid fibrillization encompasses a decrease in amyloid expression, including transcription, translation, or both, and also encompasses promoting the degradation of amyloid, including at the RNA level (e.g., RNAi, shRNA, etc.) and at the protein level (e.g., degredation, etc.) The skilled artisan will also appreciate, once armed with the teachings of the present invention, that a decrease in amyloid fibrillization includes a decrease in a amyloid activity (e.g., enzymatic activity, substrate binding activity, receptor binding activity, etc.). Thus, decreasing amyloid fibrillization includes, but is not limited to, decreasing transcription, translation, or both, of a nucleic acid encoding amyloid; and it also includes decreasing any activity of a amyloid polypeptide, or peptide fragment thereof, as well. The amyloid inhibitor compositions and methods of the invention can selectively inhibit amyloid, or can inhibit both amyloid and another molecule.

Inhibition of amyloid fibrillization can be assessed using a wide variety of methods, including those disclosed herein, as well as methods known in the art or to be developed in the future. That is, a person of ordinary skill in the art would appreciate, based upon the disclosure provided herein, that decreasing the level or activity of amyloid can be readily assessed using methods that assess the level of a nucleic acid encoding amyloid (e.g., mRNA), the level of a amyloid polypeptide, or peptide fragment thereof, present in a biological sample, the level of amyloid activity (e.g., enzymatic activity, substrate binding activity, receptor binding activity, etc.), or combinations thereof.

One skilled in the art, based upon the disclosure provided herein, would understand that the invention is useful in treating or preventing a disease or disorder in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where amyloid plays a role and where diminished amyloid fibrillization will promote a positive therapeutic outcome. The amyloid inhibitor compositions and methods of the invention that decrease the level or activity (e.g., amyloid fibrillization, etc.) of amyloid, or an amyloid fragment, include, but should not be construed as being limited to, a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, or combinations thereof. In some embodiments, the inhibitor is an allosteric inhibitor. One of skill in the art would readily appreciate, based on the disclosure provided herein, that an amyloid inhibitor composition encompasses any chemical compound that decreases amyloid fibrillization. Additionally, an amyloid inhibitor composition encompasses a chemically modified compound, and derivatives, as is well known to one of skill in the chemical arts.

Further, one of skill in the art, when equipped with this disclosure and the methods exemplified herein, would appreciate that a amyloid inhibitor composition includes such inhibitors as discovered in the future, as can be identified by well-known criteria in the art of pharmacology, such as the physiological results of inhibition of amyloid as described in detail herein and/or as known in the art. Therefore, the present invention is not limited in any way to any particular amyloid inhibitor composition as exemplified or disclosed herein; rather, the invention encompasses those inhibitor compositions that would be understood by the person of ordinary skill in the art to be useful as are known in the art and as are discovered in the future.

Further methods of identifying and producing amyloid inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, a amyloid inhibitor can be synthesized chemically. Further, the routineer would appreciate, based upon the teachings provided herein, that a amyloid inhibitor composition can be obtained from a recombinant organism. Compositions and methods for chemically synthesizing amyloid inhibitors and for obtaining them from natural sources are well known in the art and are described in the art.

One of skill in the art will appreciate that an inhibitor can be administered as a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a amyloid receptor, a amyloid receptor fragment, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of amyloid. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the level or activity of amyloid can serve in the compositions and methods of the present invention to decrease the level or activity of amyloid.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of amyloid, or to diminish the amount of a molecule that causes an increase in the amount or activity of amyloid, thereby decreasing the amount or activity of amyloid.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing amyloid, or of a gene expressing a protein that increases the level or activity of amyloid, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

Alternatively, inhibition of a gene expressing amyloid, or of a gene expressing a protein that increases the level or activity of amyloid, can be accomplished through the use of a short hairpin RNA or antisense RNA, including siRNA, miRNA, and RNAi. Given the nucleotide sequence of the molecule, one of ordinary skill in the art could synthesize such an short hairpin RNA or antisense RNA without undue experimentation, provided with the disclosure and references incorporated herein.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that an amyloid inhibitor composition, as discussed elsewhere herein, can be administered to a subject prior to the onset of the disease or disorder, thereby preventing the disease or disorder from developing.

The invention provides compositions that bind to amyloid. In one embodiment, the amyloid binding agent inhibits amyloid levels or activity. Thus, in diseases and conditions where a reduction of amyloid activity would be beneficial, such inhibitory amyloid binding agents can potentially act as therapeutics.

Anti-Amyloid Antibodies

Antibodies, including amyloid binding fragments thereof, of the present invention include, in certain embodiments, antibody amino acid sequences disclosed herein encoded by any suitable polynucleotide, or any isolated or formulated antibody. Further, antibodies of the present disclosure comprise antibodies having the structural and/or functional features of anti-amyloid antibodies described herein. In one embodiment, the anti-amyloid antibody binds amyloid and, thereby partially or substantially alters at least one biological activity of amyloid (e.g., amyloid fibrillization). In some embodiments, the amyloid is a microbial amyloid.

In one embodiment, anti-amyloid antibodies of the invention immunospecifically bind at least one specified epitope specific to the amyloid protein, peptide, subunit, fragment, portion or any combination thereof and do not specifically bind to other polypeptides, other than amyloid from other species. The at least one epitope can comprise at least one antibody binding region that comprises at least one portion of the amyloid protein. The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The invention provides an immunological composition comprising at least one antibody having pan-amyloid binding activity. For example, in one embodiment, the composition comprises an antibody or antibody fragment that specifically binds to a beta sheet structure of an amyloid protein. Exemplary anti-amyloid antibodies include, but are not limited to, ALZ.3H3, ALZ.2C10, ALZ.4G1, and ALZ.4A6.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

Methods of making and using antibodies are well known in the art. For example, polyclonal antibodies useful in the present invention can be generated by immunizing rabbits according to standard immunological techniques well-known in the art (see, e.g., Harlow et al., 1988, In: Antibodies, A Laboratory Manual, Cold Spring Harbor, NY). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, NY).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody may have a half-life within the subject. In some embodiments, the antibody may be modified to extend or shorten its half-life within the subject. The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

The antibody can be defucosylated. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. The antibody may be modified so as to prevent or inhibit fucosylation of the antibody. The modification may be in the heavy chain, light chain, or a combination thereof. The modification may be one or more amino acid substitutions in the heavy chain, one or more amino acid substitutions in the light chain, or a combination thereof.

The anti-amyloid antibody can treat, prevent, and/or protect against disease in the subject administered the composition. The anti-amyloid antibody can promote survival of the disease in the subject administered the composition. In one embodiment, the anti-amyloid antibody can provide increased survival of the disease in the subject over the expected survival of a subject having the disease who has not been administered the anti-amyloid antibody. In various embodiments, the anti-amyloid antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition.

In one embodiment, the anti-amyloid antibody can provide increased protection against the disease in the subject over the expected protection of a subject who has not been administered the anti-amyloid antibody. In various embodiments, the anti-amyloid antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

Combination with Antibiotic Treatment

In one aspect, the present invention provides a composition comprising an anti-amyloid antibody of the invention in combination with at least one additional agent. In one embodiment, the additional agent is an antibiotic. In one aspect, the present invention provides a composition comprising an anti-amyloid antibody of the invention and an antibiotic treatment. In one embodiment, the weight ratio between an anti-amyloid antibody of the invention and an antibiotic treatment is from about 10:1 to about 1:10. In one embodiment, the weight ratio between an anti-amyloid antibody of the invention and an antibiotic treatment is from about 4:1 to about 1:4. In one embodiment, the weight ratio between an anti-amyloid antibody of the invention and an antibiotic treatment is from about 2:1 to about 1:2. In one embodiment, the weight ratio between an anti-amyloid antibody of the invention and an antibiotic treatment is about 1:1, about 1:2, about 1:3, about 1:4, about 1:5, about 2:1, about 3:1, about 4:1, or about 5:1. In one embodiment, the total concentration of an anti-amyloid antibody of the invention and an antibiotic treatment in the composition of the present invention is from about 1 wt. % to about 50 wt. %. In one embodiment, the total concentration of an anti-amyloid antibody of the invention and an antibiotic treatment in the composition of the present invention is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the composition.

Pharmaceutical Compositions and Formulations

The invention also encompasses a pharmaceutical composition comprising an antibody having pan-amyloid activity. In one embodiment, the pharmaceutical composition is useful for inhibiting bacterial infections. In one embodiment, the pharmaceutical composition is useful for overcoming antibacterial resistance. Such a pharmaceutical composition may consist of an antibody having pan-amyloid activity in a form suitable for administration to a subject. In one embodiment, the composition of the invention may comprise a nucleic acid molecule encoding an antibody having pan-amyloid activity.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of an antibody having pan-amyloid activity and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

The compositions of the invention may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In one embodiment, the composition is an antimicrobial composition. In one embodiment, the composition is an antiseptic.

The compositions useful within the invention may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, the compound of the invention and the at least one additional antimicrobial agent act synergistically in preventing, reducing or treating bacterial infections. A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The compositions of the invention can be formulated as appropriate for topical administration, Accordingly the present invention provides the use of a topical formulation for treating a microbial infection, or for decolonizing a microbial organism, or for destroying or disrupting or inhibiting or reducing biofilm formation of a microbial organism, said topical formulation comprises an anti-amyloid antibody of the invention.

In one embodiment, the topical formulation of the present invention may take the form of a cream, a lotion, an ointment, a hydrogel, a colloid, a gel, a foam, an oil, a milk, a suspension, a wipe, a sponge, a solution, an emulsion, a paste, a patch, a pledget, a swab, a dressing, a spray or a pad.

The topical formulation of the present invention comprises one or more pharmaceutically acceptable carrier. Examples of the pharmaceutically acceptable carriers that are usable in the context of the present invention include carrier materials such as a solvent, a stabilizer, a solubilizer, a filler, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof.

Examples of solvents are water or purified water, alcohols (e.g., ethanol, benzyl alcohol), vegetable, marine and mineral oils, polyethylene glycols, propylene glycols, glycerol, and liquid polyalkylsiloxanes.

Inert diluents or fillers may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (i.e., tris(hydroxymethyl)aminomethane hydrochloride).

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a topical composition of the invention to prevent microbial contamination that can affect the stability of the formulation and/or cause infection in the patient. Suitable examples of preservatives include parabens (such as methyl, ethyl, propyl, /p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol.

Examples of chelating agents include sodium EDTA and citric acid.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates.

Ointment bases suitable for use in the compositions of the present invention may be hydrophobic or hydrophilic. Ointment bases include, but are not limited to, paraffin, lanolin, liquid polyalkylsiloxanes, cetanol, cetyl palmitate, vegetal oils, sorbitan esters of fatty acids, polyethylene glycols, and condensation products between sorbitan esters of fatty acids, ethylene oxide (e.g., polyoxyethylene sorbitan monooleate), polysorbates, white petrolatum and white wax.

Examples of humectants include, but are not limited to, ethanol, isopropanol glycerin, propylene glycol, sorbitol, lactic acid, and urea. Suitable emollients include cholesterol and glycerol.

Examples of skin protectants include, but are not limited to, vitamin E, allatoin, glycerin, zinc oxide, vitamins, and sunscreen agents.

Thickening agents are generally used to increase viscosity and improve bioadhesive properties of pharmaceutical or cosmetic compositions. Examples of thickening agents include, but are not limited to, celluloses, polyethylene glycol, polyethylene oxide, naturally occurring gums, gelatin, karaya, pectin, alginic acid, povidone, and Carbopol® polymers. Particularly interesting are thickening agents with thixotropic properties (i.e., agents whose viscosity is decreased by shaking or stirring). The presence of such an agent in a composition allows the viscosity of the composition to be reduced at the time of administration to facilitate its application to the skin and, to increase after application so that the composition remains at the site of administration.

Bioadhesive polymers are useful to hydrate the skin and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include, but are not limited to, alcohols (e.g., ethyl alcohol, isopropyl alcohol), dimethyl formamide, dimethyl acetamide, dimethyl sulfoxide, 1-dodecylazocyloheptan-2-one, N-decyl-methylsulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. Surfactant permeation enhancing agents may be nonionic, amphoteric, cationic, or zwitterionic. Suitable nonioinic surfactants include, but are not limited to, poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, and zwitterionic surfactants include the betaines and sulfobetaines. Other examples of suitable permeation enhancers include pentadecalactone, 2-pyrrolidine, 1-dodecal-azacycloheptane-2-one, calcium thioglycolate, hexanol, derivatives of 1,3-dioxanes (i.e., 1,3-dioxacyclohexanes) and 1,3-dioxalanes (i.e., 1,3-dioxacyclopentanes), 1-N-dodecyl-2-pyrrolidone-5-carboxylic acid, 2-pentyl-2-oxo-pyrrolidineacetic acid, 2-dodecyl-2-oxo-1-pyrrolidineacetic acid, and 1-azacycloheptan-2-one-2-dodecylacetic acid among others.

Medical Devices

The invention contemplates applying to or coating medical devices with the compositions useful within the invention. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the invention is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In one specific embodiment, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In one embodiment, the biofilm-penetrating composition is applied to the entire medical device.

Administration

The present invention provides the use of an anti-amyloid antibody of the invention for treating a microbial infection, or for decolonizing a microbial organism, or for destroying or disrupting or inhibiting or reducing biofilm formation of a microbial organism.

In one embodiment, the composition described herein is for administration to a subject. In one embodiment the subject has microbial infection or colonization by microbes. Preferably the microbial infection or colonization site is characterized with microbial colonies or biofilm or biofilm formation. Preferably the microbial infection is a bacterial infection. In one embodiment, the bacteria infection is from Gram-positive or Gram-negative bacteria. In one embodiment the bacterial infection is from one selected from *Staphylococcus* spp., e.g. *Staphylococcus aureus*, *Staphylococcus epidermidis*; *Enterococcus* spp., e.g. *Enterococcus faecalis*; *Klebsiella* spp., e.g. *Klebsiella pneumoniae*; *Acinetobacter* spp., e.g. *Acinetobacter baumannii*; *Pseudomonas* spp., e.g. *Pseudomonas aeruginosa*; *Enterobacter* spp.; *Streptococcus pyogenes*; *Listeria* spp.; *Pseudomonas* spp.; *Mycobacterium* spp., e.g. *Mycobacterium tuberculosis*; *Enterobacter* spp.; *Campylobacter* spp.; *Salmonella* spp.; *Streptococcus* spp., e.g. *Streptococcus* Group A or B, *Streptoccocus pneumoniae*; *Helicobacter* spp., e.g. *Helicobacter pylori*; *Neisseria* spp., e.g. *Neisseria gonorrhea*, *Neisseria meningitidis*; *Borrelia burgdorferi*; *Shigella* spp., e.g. *Shigella flexneri*; *Escherichia coli*; *Haemophilus* spp., e.g. *Haemophilus influenzae*; *Chlamydia* spp., e.g. *Chlamydia trachomatis*, *Chlamydia pneumoniae*, *Chlamydia psittaci*; *Francisella fularensis*; *Bacillus* spp., e.g. *Bacillus anthracis*; *Clostridia* spp., e.g. *Clostridium botulinum*; *Yersinia* spp., e.g. *Yersinia pestis*; *Treponema* spp.; *Burkholderia* spp.; e.g. *Burkholderia mallei* and *B. pseudomallei*, or the combination thereof. Also in one embodiment, the bacteria are selected from *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, ifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtherias, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Finegoldia magna, Geobacillus kaustophilus, Geobacillus thermodenitrificans, Janibacter* sp., *Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp., *Nocardia farcinica, Oceanobacillus iheyensis, Pelotomaculum thermopropionicum, Rhodococcus* sp., *Saccharopolyspora erythraea*, coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis*, (MRSE), *Staphylococcus pseudintermedius, Staphylococcus intermedius, Staphylococcus delphini, Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis*, or the combination thereof.

In one embodiment, the biofilm formation is on a surface of a device. In one embodiment, the device is a medical device. In one embodiment, the biofilm formation is on a surface of or in a tissue of a subject. In one embodiment, the biofilm formation is on a skin, eye, a mucous membrane, surface of cavity, etc.

Accordingly the present invention provides the use of a composition comprising an anti-amyloid antibody of the invention for treating a microbial infection, or for decolonizing a microbial organism, or for destroying or disrupting or inhibiting or reducing biofilm formation of a microbial organism. In one embodiment, the use is for decolonizing a microbial organism, or for disrupting or inhibiting or reducing biofilm formation on a surface of a medical device.

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the disease or infection in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the composition of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a composition of the invention is from about 1 mg to about 2,500 mg. In some embodiments, a dose of a composition of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second composition as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compositions for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compositions lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a composition of the invention, alone or in combination with a second pharmaceutical agent; and instructions for using the composition to treat or prevent a disease or infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compositions for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Routes of Administration

Routes of administration of any of the compositions of the invention include oral, rectal, transdermal, transmucosal (e.g., sublingual, lingual, (trans)buccal, (trans)urethral, vaginal (e.g., trans- and perivaginally), (trans)rectal, intravesical, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a composition through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active composition should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compositions may be synthetically—or naturally derived.

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compositions of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compositions may be formulated with a suitable polymer or hydrophobic material which provides sustained release properties to the compositions. As such, the compositions for use the method of the invention may be administered in the form of microparticles, for example, by injection or in the form of wafers or discs by implantation.

In one embodiment of the invention, the compositions of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Combination Therapy

The anti-amyloid antibody of the present invention may be administered alone or in conjunction with another therapy. For example, the combination therapy of the present invention may be used in conjunction with a disinfectant, antiseptic, antibiotic, or biocide on a surface such as medical devices and indwelling devices including stents, catheters, peritoneal dialysis tubing, draining devices, joint prostheses, dental implants and the like.

In one embodiment, the present invention provides a synergistic combination therapy comprising an anti-amyloid antibody of the invention and an antibiotic treatment that can be administered topically for the treatment of a microbial colonized surface or infection.

In another aspect, the present invention provides a method of treating a microbial infection in a subject comprising administering to the subject separately, simultaneously or sequentially a therapeutically effective amount of an anti-amyloid antibody of the invention and an antibiotic treatment. In one embodiment, the method comprises administering to the subject a therapeutically effective amount of a composition comprising an anti-amyloid antibody of the invention and an antibiotic treatment described herein. In one embodiment, the method comprises administering to the subject a therapeutically effective amount of a topical formulation comprising an anti-amyloid antibody of the invention and an antibiotic treatment described herein and one or more pharmaceutically acceptable carriers or excipients, wherein the topical formulation and the pharmaceutically acceptable carriers or excipients are defined herein throughout the specification. In one embodiment, the infection is a topical infection. The topical infection is an infection on a surface or localized region of a subject including skin, eye, a mucous membrane, a surface of cavity, etc.. In one embodiment, the topical infection is the infection on the skin. In one embodiment, the topical infection is in the form of wound, ulcer and lesion. In one embodiment, the microbial organism is a bacterium.

In one embodiment, the present invention provides a method of decolonizing a microbial organism comprising contacting the microbial organism separately, simultaneously or sequentially with an anti-amyloid antibody of the invention and an antibiotic treatment. In one embodiment, the method comprises contacting the microbial organism with a composition comprising an anti-amyloid antibody of the invention and an antibiotic treatment described herein. In one embodiment, the method comprises contacting the microbial organism with a topical formulation comprising an anti-amyloid antibody of the invention and an antibiotic treatment described herein and one or more pharmaceutically acceptable carriers or excipients, wherein the topical formulation and the pharmaceutically acceptable carriers or excipients are defined herein throughout the specification. According to any of the methods describes herein, the microbial organism is a bacterium.

In one embodiment, the biofilm formation is on a surface of a device. In one embodiment, the device is implanted catheters, prosthetic heart valves, cardiac pacemakers, contact lenses, cerebrospinal fluid shunts, joint replacements or intravascular lines. In one embodiment, the biofilm formation is on a surface of or in a tissue of a subject. In one embodiment, the biofilm formation is on a skin, eye, a mucous membrane, surface of cavity, etc..

In one embodiment, the present invention provides a method of destroying or disrupting or inhibiting or reducing biofilm formation of a microbial organism comprising contacting the microbial organism separately, simultaneously or sequentially with a composition comprising an anti-amyloid antibody of the invention and a composition comprising an antibiotic. In one embodiment, the method comprises contacting the microbial organism with a composition comprising an anti-amyloid antibody of the invention and an antibiotic described herein. In one embodiment, the method comprises contacting the microbial organism with a topical formulation comprising an anti-amyloid antibody of the invention and an antibiotic treatment described herein and one or more pharmaceutically acceptable carriers or excipients, wherein the pharmaceutically acceptable carriers or excipients are defined herein throughout the specification. In one embodiment, the microbial organism is a bacterium.

These methods described herein are by no means all inclusive, and further methods to suit the specific application will be apparent to the ordinary skilled artisan. Moreover, the effective amount of the compositions can be further approximated through analogy to compositions known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Anti-Amyloid Directed Monoclonal Antibodies Reduce Biofilm Formation of *Salmonella Typhimurium* by Targeting Amyloid Curli Amyloids from prokaryotic and eukaryotic origin do not share primary sequence structure, however amyloids from both lineages share a common conserved beta sheet structure (Rapsinski et al., 2013, J Biol Chem, 17; 288(20):14178-88). Furthermore both bacterial and host amyloids bind to and activate TLR2. Similar to the binding of curli to TLR2 on innate immune cells (Tiikel et al., 2010, Cell Microbiol, 12(10):1495-505), binding of amyloid beta associated in Alzheimer's disease (Liu et al., 2012, J Immunol, 188(3): 1098-107; Udan et al., 2008, J Neurochem, 104(2):524-33) and Serum Amyloid A in atherosclerosis (Seidl et al., 2017, PLoS One, 12(3):e0171711). The ability of the monoclonal antibodies to bind to and inhibit the fibrillization of bacterial amyloid curli implicated in biofilm formation was tested. Using a multi-disciplinary approach, various human monoclonal antibodies were identified that exhibit reactivity against amyloid-β that as well exhibit anti-curli properties within the context of *S. Typhimurium* biofilms. Incubation of *S. Typhimurium* (STM) biofilms with the mAb altered the biofilm architecture, destabilized the biofilm and ultimately reduced biomass. The resulting alterations to the biofilm architecture and stability rendered the biofilm more sensitive to treatment with antibiotics, DNase and macrophage uptake of bacteria in comparison to biofilms that did not receive mAb treatment. Overall, a novel therapeutic method has been identified by which targeting curli within the biofilm of *S. Typhimurium* biofilms through the use of anti-amyloid mAbs results in alterations in biofilm architecture, stability and overall result in reduction of the biofilm.

The experimental methods and results are now described.
Monoclonal Antibody ALZ.3H3 Disrupts *S. Typhimurium* Biofilm Architecture and Integrity Biofilms were established in the presence of 0.5 mg/ml ALZ.3H3 for 72 hours at 28° C. After growth, biofilms were stained with Syto9 and imaged using CSLM. Three dimensional architecture was examined by creating 3D surface plots using ImageJ. Incubation of the monoclonal antibody ALZ.3H3 altered the architecture of biofilm forming a disperse biofilm topography that expanded above the mean thickness (20 µM) of a wild-type *S. Typhimurium* biofilm which displayed a dense and compact architecture (FIG. 1A). This loose matrix was also observed in the anti-csg treatment, while biofilms treated with control A6 remained intact and undisrupted (FIG. 1A). To quantify the disperse biofilm created by treatment with ALZ.3H3, through the use of ImageJ all particles above the thickness of a wild-type *S.*

Figure 1B:
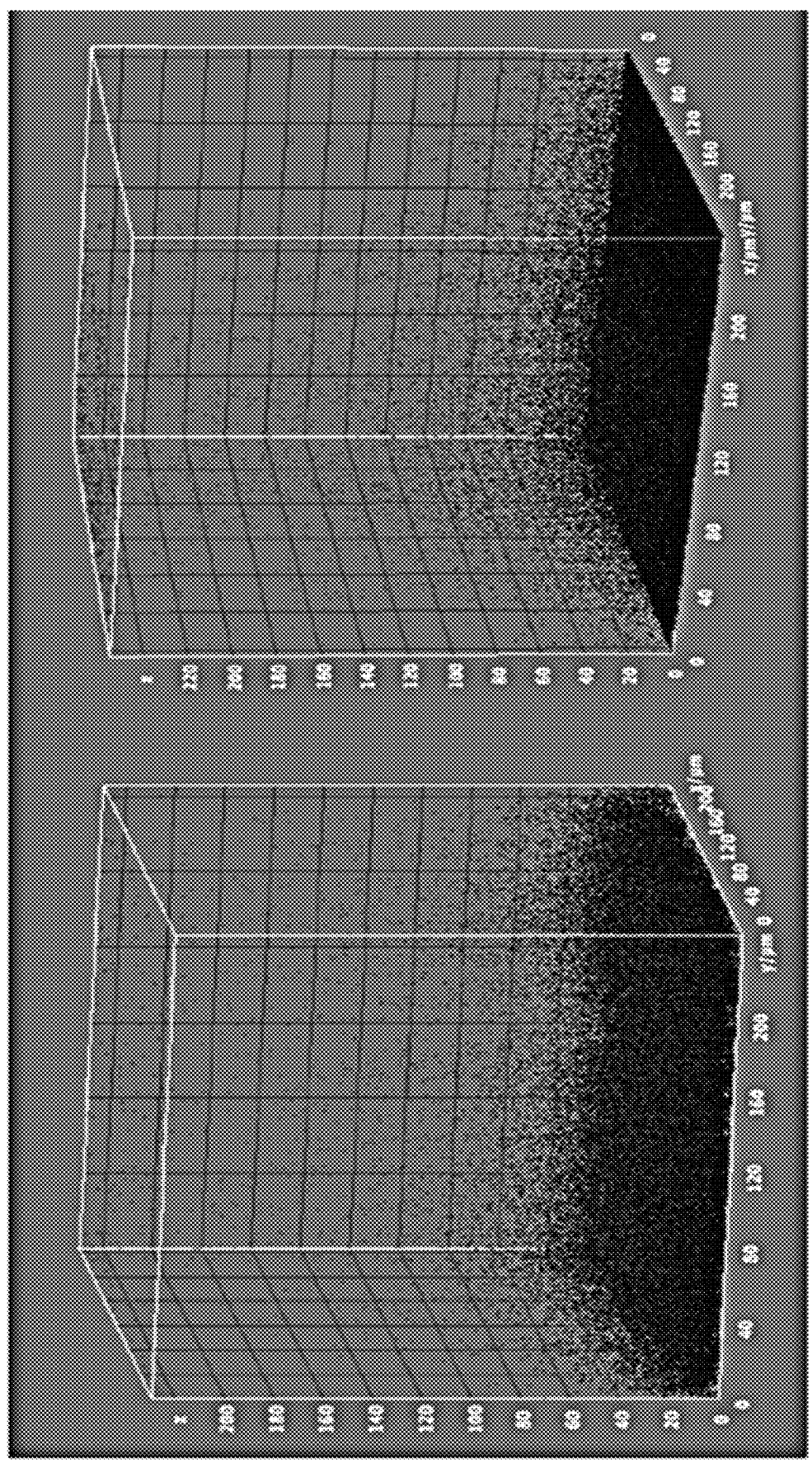
Figure 1B:
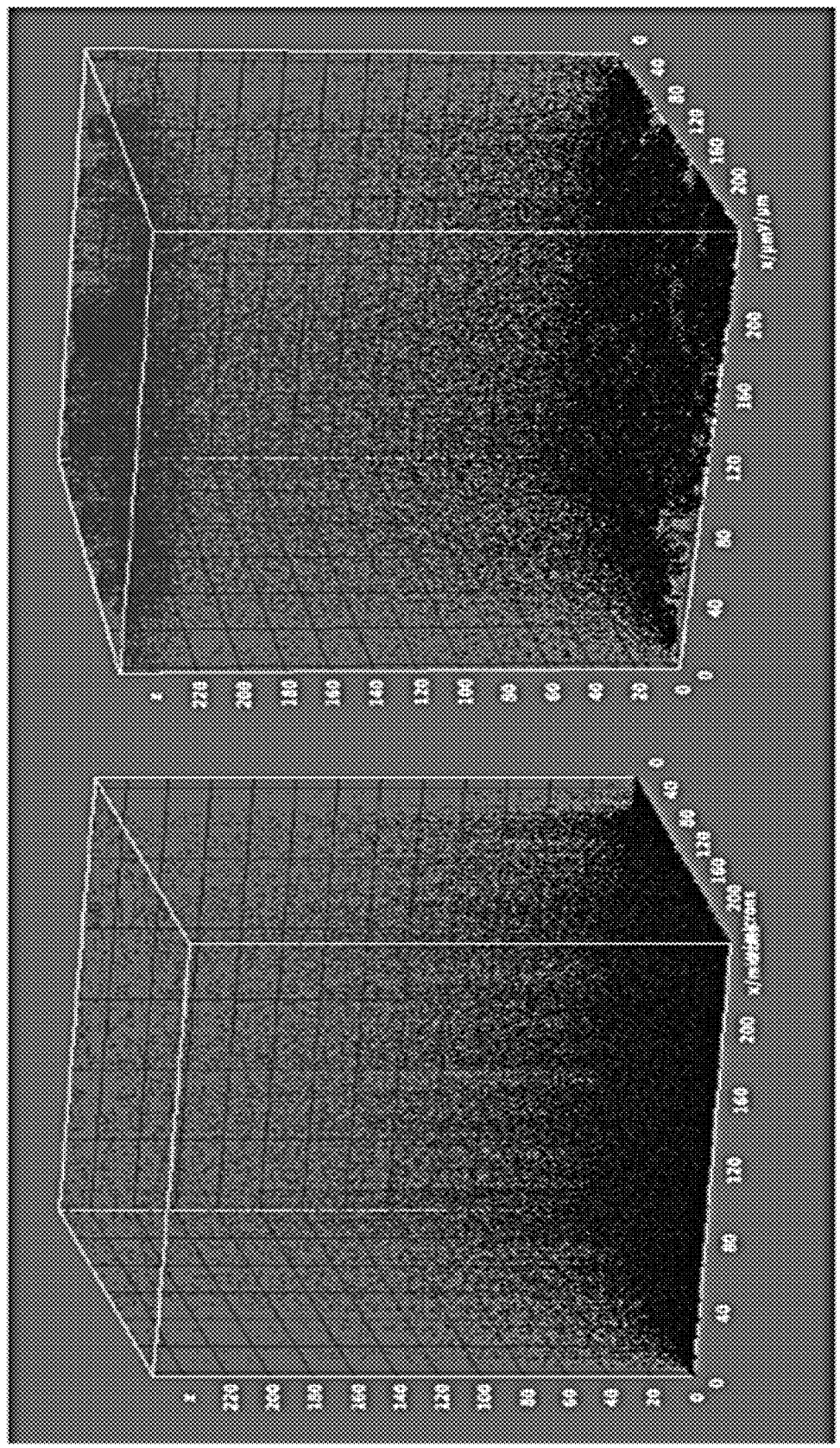
Figure 1C:
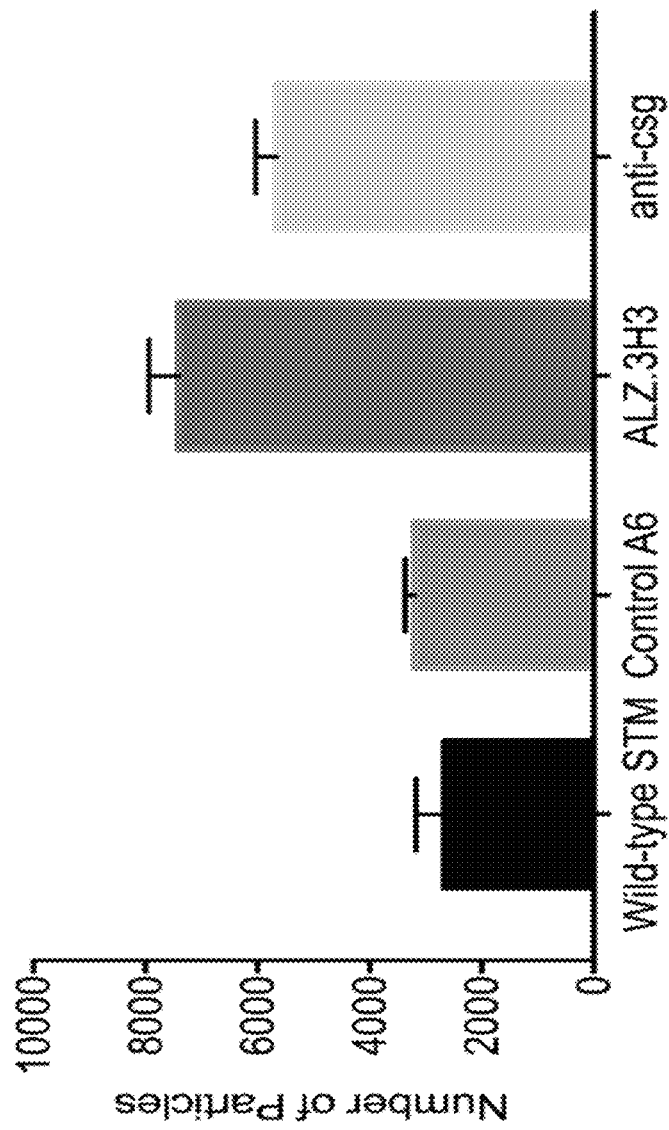

Typhimurium (20 µM) was used to set the threshold value, and these threshold parameters were applied to subsequent treatments (FIG. 1B). Upon enumeration of the particles, there was a significant increase in number of particles upon treatment with ALZ.3H3 (FIG. 1C). To this effect, by plating supernatants recovered from the biofilms, significantly more bacteria was recovered from the biofilm supernatant of ALZ.3H3. The bacteria recovered from the supernatants is representative of the loose disperse biofilm matrix that is easily dissociated from the biomass. Overall, this data suggests that incubation with ALZ.3H3 altered the biofilm structure by disrupting the overall biofilm matrix structure.

Figure 2A:
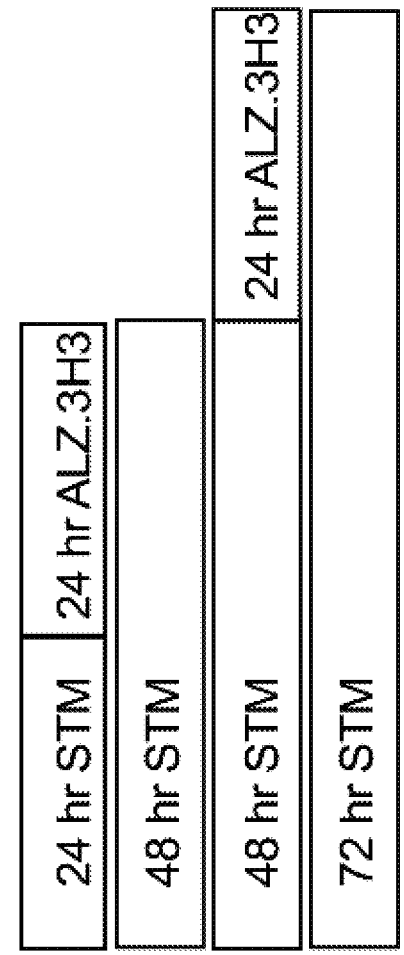
FIG. 2A through FIG. 2C depict exemplary experimental results demonstrating that the monoclonal antibody ALZ.3H3 alters biofilm integrity of pre-established *S. Typhimurium* biofilms.
Figure 2B:
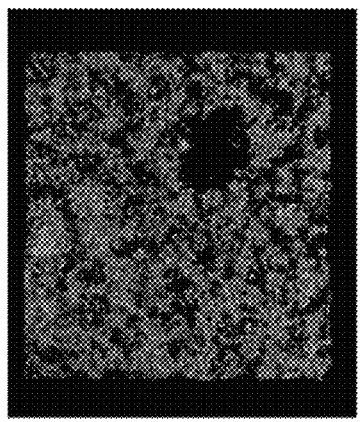
Figure 2B:
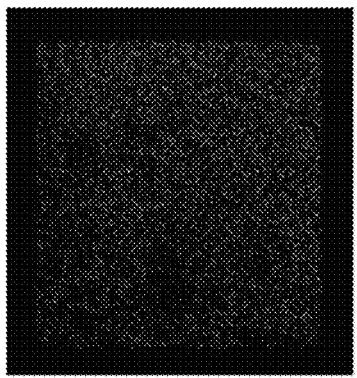
Figure 2B:
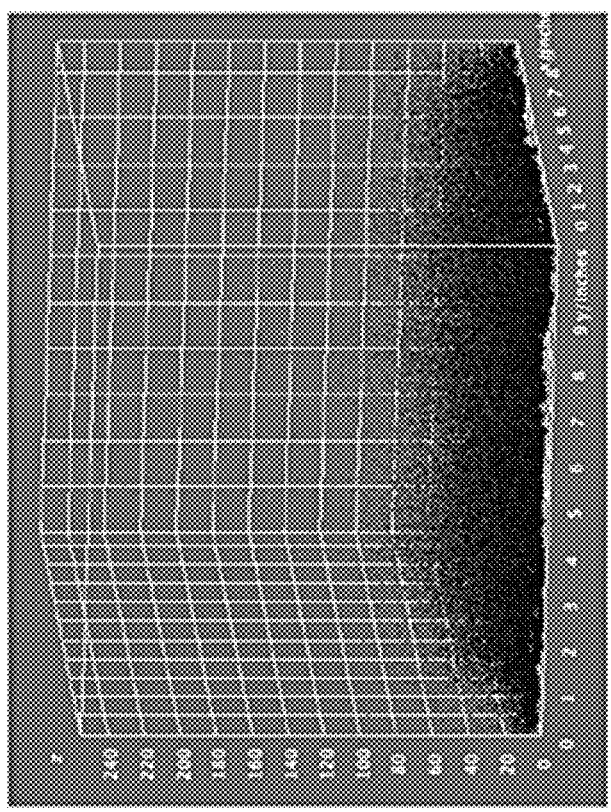
Figure 2B:
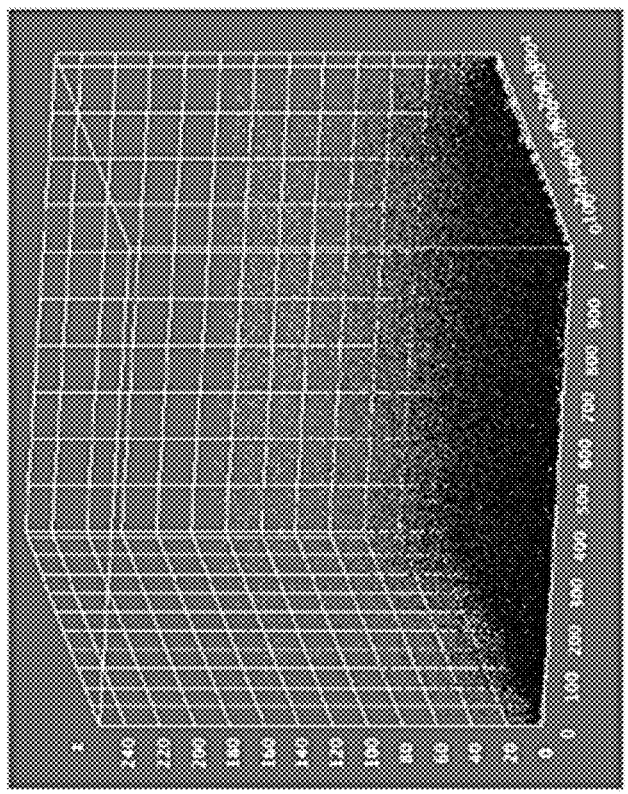
Figure 2B:
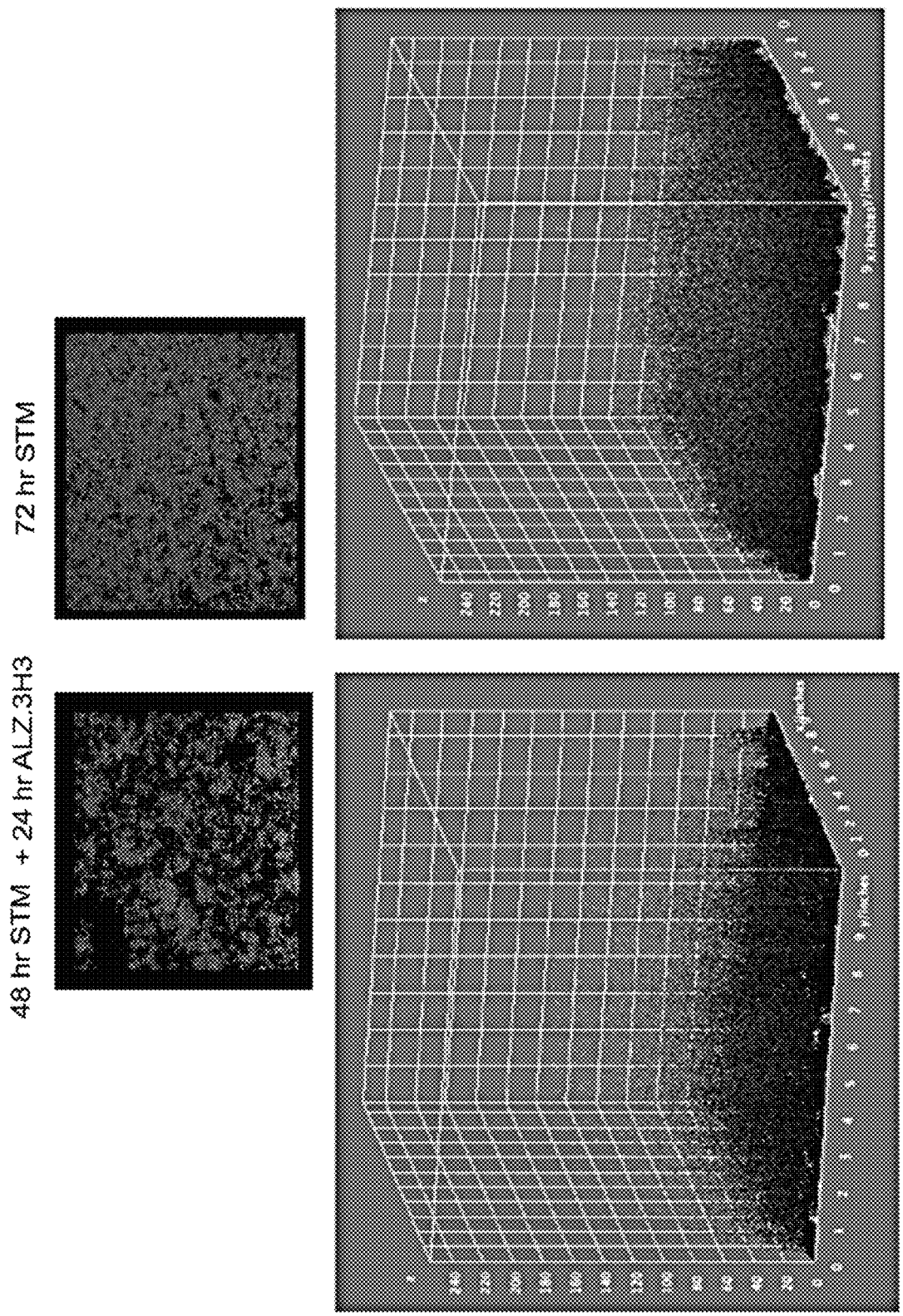
Figure 2C:
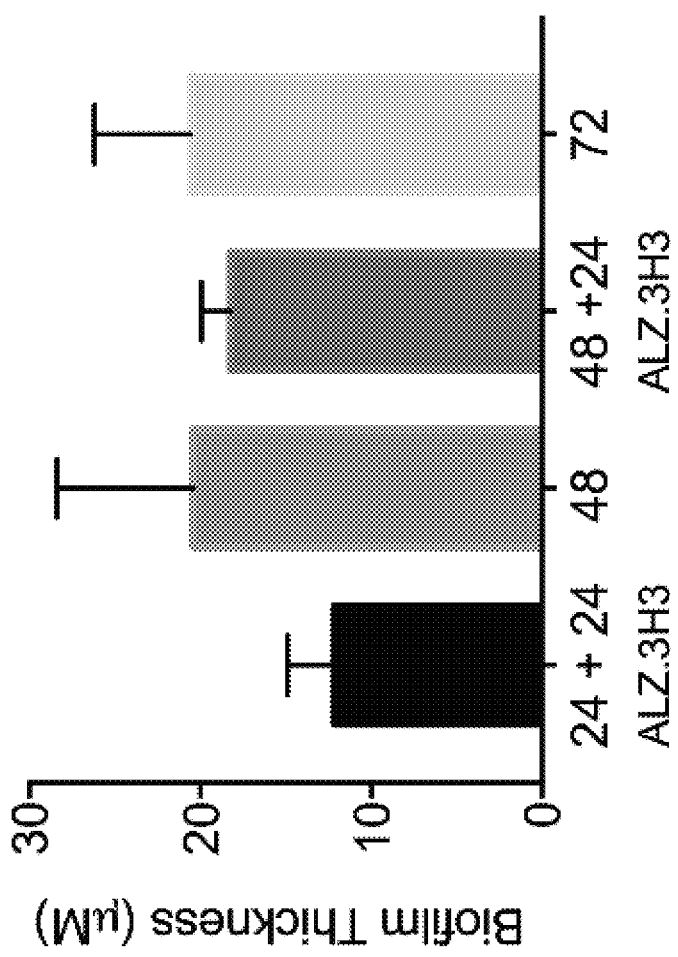

Monoclonal Antibody ALZ.3H3 Alters Biofilm Integrity of Pre-Established *S. Typhimurium* Biofilms To determine if ALZ.3H3 can reduce biofilm formation of pre-established biofilms of *S. Typhimurium*, 0.5 mg/ml of ALZ.3H3 was added for an additional 24 hours to a 24 hour pre-established biofilm of *S. Typhimurium*, or 0.5 mg/ml of ALZ.3H3 was added for 24 hours to a 48 hour pre-established biofilms. These biofilms were then compared, respectively, to a 48 and 72 hour *S. Typhimurium* biofilm that was not exposed to ALZ.3H3 (FIG. 2A). Biofilms were stained with Syto9 and imaged using CSML. Biofilms were not wash extensively in order determine the impact of ALZ.3H3 on biofilm architecture. In comparison to a 48 hour biofilm of wild-type *S. Typhimurium*, although still establishing and the biofilm matrix was incomplete, the 24 hours pre-established biofilm that was exposed to ALZ.3H3 for an additional 24 hours began to exhibit a more disperse matrix in comparison to the 48 hour biofilm was compact (FIG. 2B). This trend continued when a 48 hour pre-established biofilm was incubated for an additional 24 hours with 0.5 mg/ml ALZ.3H3 where the biofilm matrix was more disperse in comparison to the 72 hour fully formed *S. Typhimurium* biofilm that did not receive ALZ.3H3 treatment (FIG. 2B). Using the thresholding technique described earlier, the number of particles above the thickness of the wild-type *S. Typhimurium* were counted. Even as early as 24 hours, incubation with ALZ.3H3 increased the number of particles above the wild-type *S. Typhimurium*, and the number of particles increased as well when a 48 hour pre-established biofilm of *S. Typhimurium* was incubated with ALZ.3H3 for 24 hours (FIG. 2C). This data suggests that ALZ.3H3 impacts the structure pre-established biofilms of *S. Typhimurium* as early as 24 hours after addition of ALZ.3H3.

Dosage Response of ALZ.3H3 on Biofilm Integrity

Figure 3:
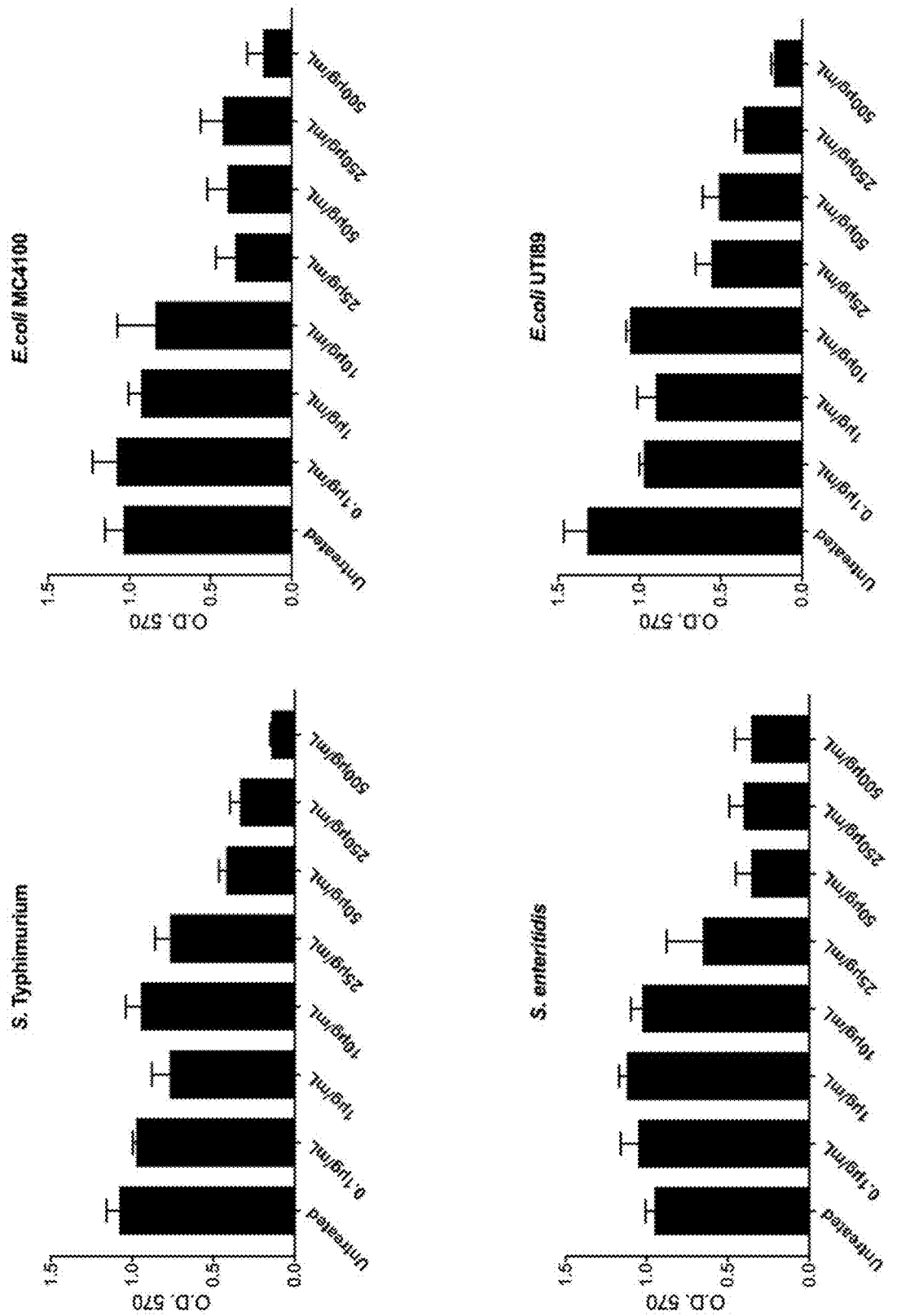
FIG. 3 depicts a crystal violet assay dose curve of ALZ.3H3.

A crystal violet assay dose curve of 3H3 (0.1 ug/ml, 1 ug/ml, 10 ug/ml, 25 ug/ml, 50 ug/ml, 250 ug/ml 500 ug/ml and untreated) added during biofilm growth of *S. Typhimurium*, *E. coli* MC4100, *S. enteritidis* and *E. coli* UTI89 was performed and the biomass determined at absorbance at 570 nm (FIG. 3).

Figures 4A, 4B:
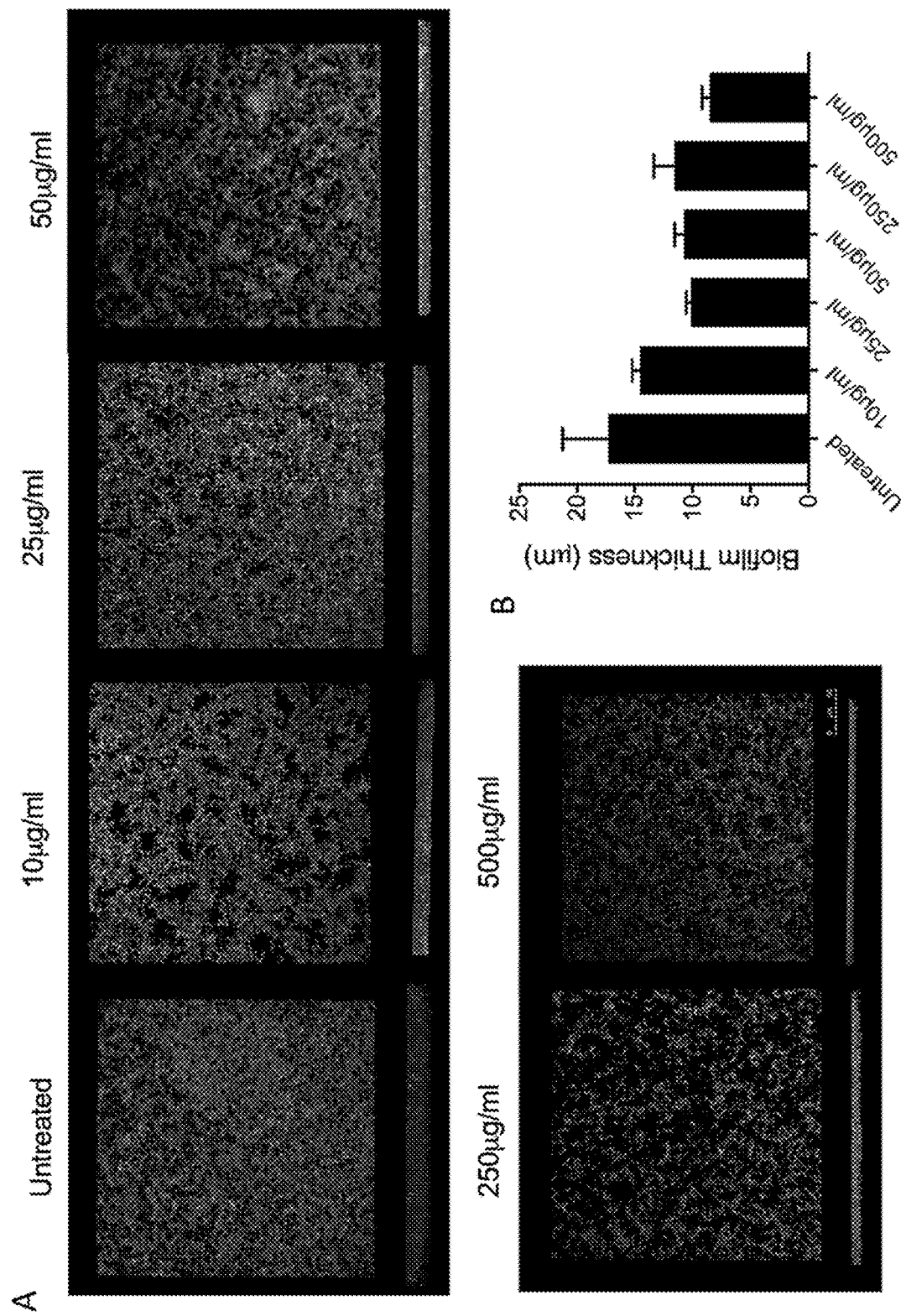
FIG. 4A and FIG. 4B depict analyses of biofilms of *S. Typhimurium*.

Confocal analysis of biofilms of *S. Typhimurium* grown in the presence (10 ug/ml, 25 ug/ml, 50 ug/ml, 250 ug/ml, 500 ug/ml) or absence (untreated) of 3H3 were performed. Biofilms were stained with syto9 (green nucleic acid stain for bacteria) and amyloid dye Congo red (red curli) and were imaged using Leica TCS confocal at 63×. Biofilm 3D reconstructions created using ImageJ 3D viewer software (FIG. 4A). Biofilm thickness (um) of biofilms of *S. Typhimurium* grown in the presence (10 ug/ml, 25 ug/ml, 50 ug/ml, 250 ug/ml, 500 ug/ml) or absence (untreated) of 3H3 was measure measured using Leica TCS confocal microscopy software (FIG. 4C).

ALZ.3H3 Reduces Fibrillization of Curli.

Figures 5A, 5B:
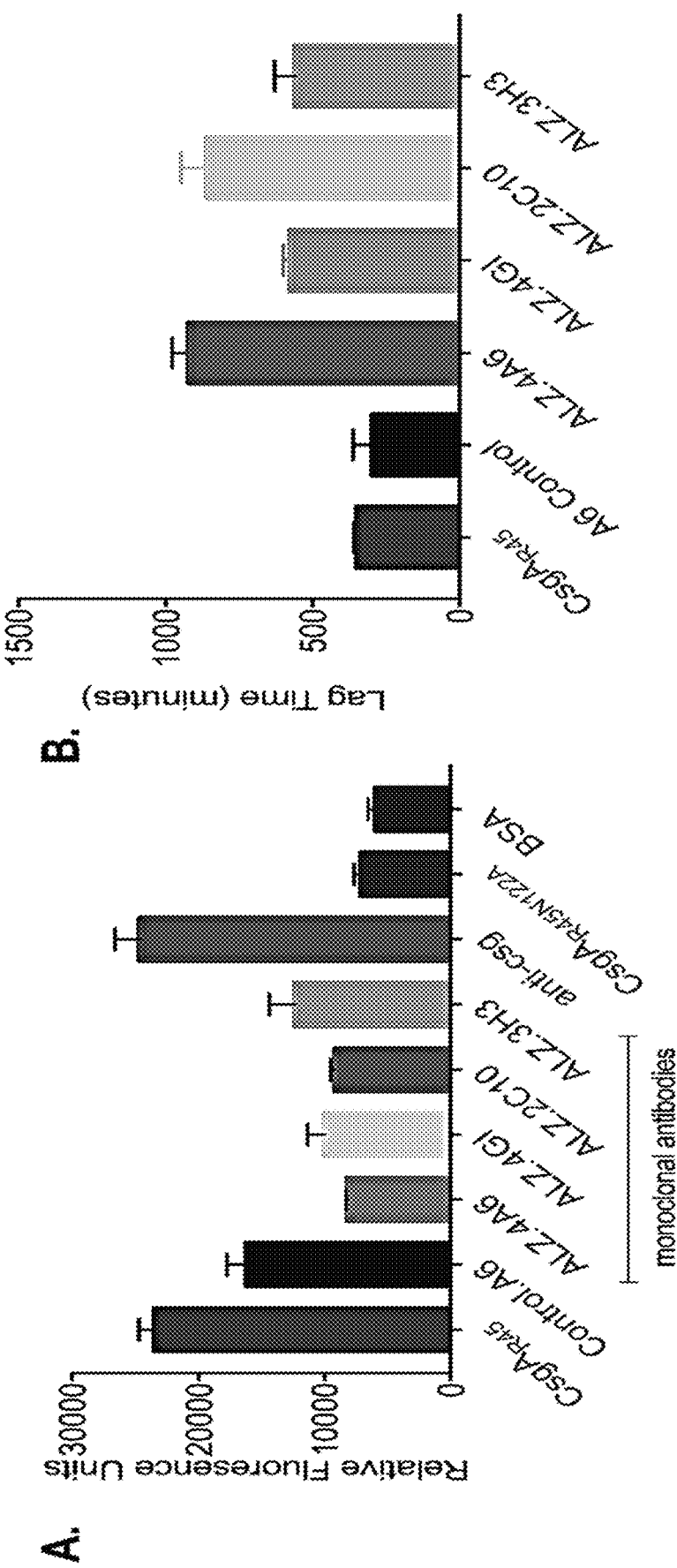
FIG. 5A through FIG. 5B depict exemplary experimental results demonstrating that ALZ.3H3 reduces fibrillization of curli.

The formation of monomers into mature curli fibrils can be monitored by incubation with Thioflavin T (ThT). Fluorescence of ThT increases as it binds to amyloid fibril, allowing the amyloid formation process to be measured spectroscopically. The formation of amyloid fibers can be defined by a three stage sigmoidal curve (Dueholm et al., 2011, Biochemistry, 50(39):8281-90; Wang et al., 2007, J Biol Chem, 282(6):3713-9). In the first stage, monomeric subunits are slow to self-associate and ThT fluorescence is minimal (Naiki et al., 1991, Lab Invest, 65(1):104-10). The reaction exponential increases as monomeric seeds oligomerize and continue to elongate (Naiki et al., 1991, Lab Invest, 65(1):104-10). This process is marked by a rapid increase in ThT fluorescence (Naiki et al., 1991, Lab Invest, 65(1):104-10). The oligomers elongate into mature fibrils and Tht fluorescence peaks (Dueholm et al., 2011, Biochemistry, 50(39):8281-90; Wang et al., 2007, J Biol Chem, 282(6):3713-9). This reaction plateaus once all monomers have been consumed and fibril elongation ceases (Naiki et al., 1991, Lab Invest, 65(1):104-10). Histadine tagged CsgA (His-CsgA), which will naturally self-associate and fibrillize, was incubated with 0.5 mg/ml ALZ.3H3 and the fibrillization reaction was monitored using ThT. As controls synthetic peptides $CsgAR_{4-5}$ and $CsgAR_{4-5N122A}$ were incubated with Tht and the fribrillization reaction was monitored in parallel. $CsgAR_{4-5}$ is the fourth and fifth repeat of CsgA which has been shown to self-associate and form fibrils, whereas $CsgAR_{4-5N122A}$ contains a single amino acid mutation that prevents fibrillization (Tükel et al., 2009, Cell Host Microbe, 6(1):45-53). Upon fibrillization with His-CsgA and ALZ.3H3, a significant reduction in the relative fluorescence units was observed (FIG. 5A). In addition to determining the maximum relative fluorescent units that are representative of fibril formation, the lag time ($t_0$) can be calculated using the equation $t_0=t_{1/2}-2t_e$, where $t_{1/2}$ is the time required to reach half the maximum fluorescence intensity and to is the elongation time (Naiki et al., 1991, Lab Invest, 65(1):104-10). The lag time can be defined as the amount of time required for monomers to self-associate and begin to oligomerize (Naiki et al., 1991, Lab Invest, 65(1): 104-10). In comparison to the lag time calculate for the synthetic peptide $CsgAR_{4-5}$, there was a significant increase in the lag times required for His-CsgA to self-associate and oligomerize when incubated with ALZ.3H3 (FIG. 5B). Based on this data, it proposed that ALZ.3H3 interacts on the monomeric level to prevent fibrillization. By interacting with the monomer, ALZ.3H3 increases the time required for the monomers to self-associate there by preventing fibril formation.

Crystal Violet Assay of *S. Typhimurium* (STM) or *E. coli* UTI89.

Figure 6:
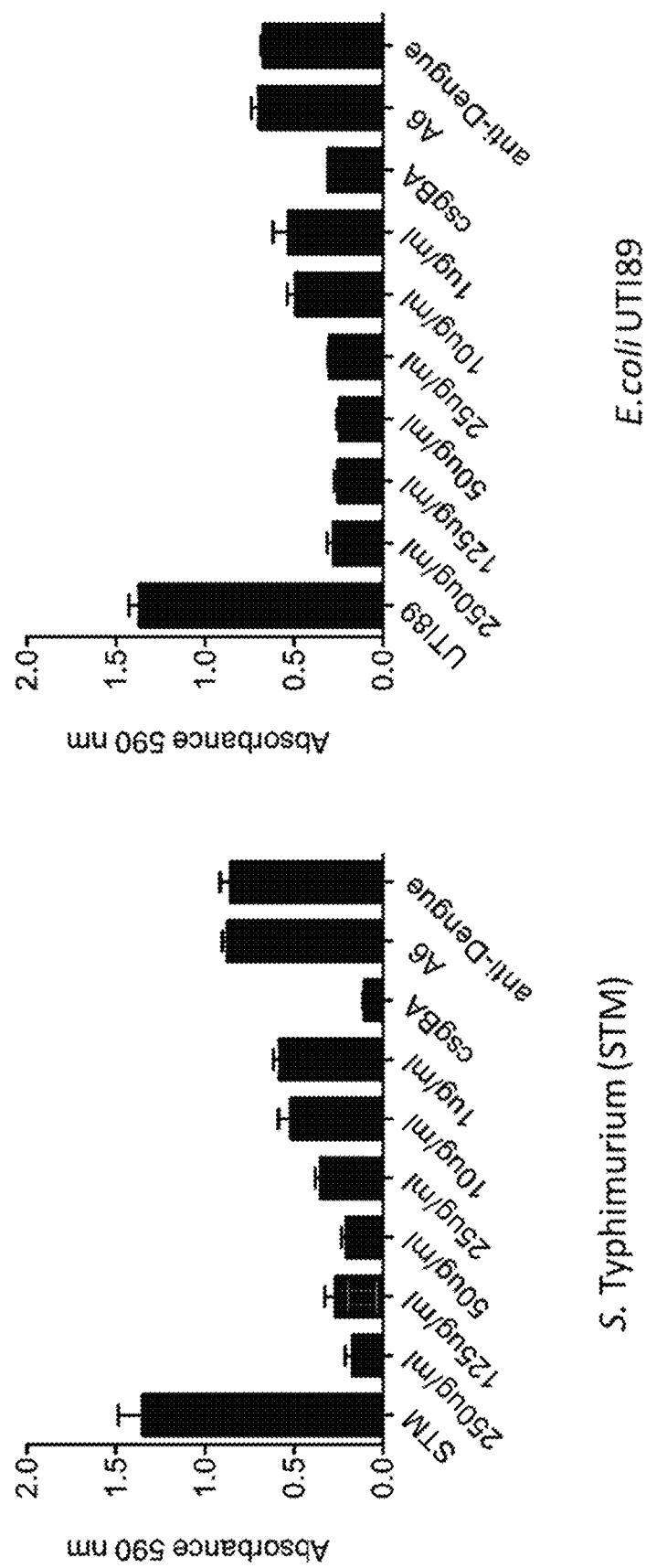
FIG. 6 depicts crystal violet assays of *S. Typhimurium* (STM) and *E. coli* UTI89. STM or UTI89 were grown in the absence or presence of 3H3 (250 ug/ml, 125 ug/ml, 50 ug/ml, 25 ug/ml, 10 ug/ml, 1 ug/ml) as well as 0.5 mg/ml control A6 or anti-Dengue antibody for 72 hours at 26 C in a sterile 96 well plate. *S. Typhimurium* curli mutant (csgBA) and UTI89 curli mutant (csgBA) were also grown as negative controls.

STM or UTI89 were grown in the absence or presence of 3H3 (250 ug/ml, 125 ug/ml, 50 ug/ml, 25 ug/ml, 10 ug/ml, 1 ug/ml) as well as 0.5 mg/ml control A6 or anti-Dengue antibody for 72 hours at 26 C in a sterile 96 well plate. *S. Typhimurium* curli mutant (csgBA) and UTI89 curli mutant (csgBA) were also grown as negative controls. More consistent results with experiments involving STM, and more variability involving experiments with UTI89 (FIG. 6).

Synergism Between ALZ.3H3 and Antibiotic Treatment Reduces *S. Typhimurium* Biofilm Formation Biofilms enhance the recalcitrance of bacteria to antibiotics (Keren et al., 2004, FEMS Microbiol Lett, 230(1):13-8, Brown et al., 1988, J Antimicrob Chemother, 22(6):777-80, Stewart, 2002, Int J Med Microbiol, 292(2):107-13). To enhance the clearance of bacterial biofilms, the structure of the biofilm was altered by employing ALZ.3H3 and then the biofilm was subjected to antibiotics to kill the bacteria within the disperse biofilm. To do this, biofilms of *S.*

Figure 7:
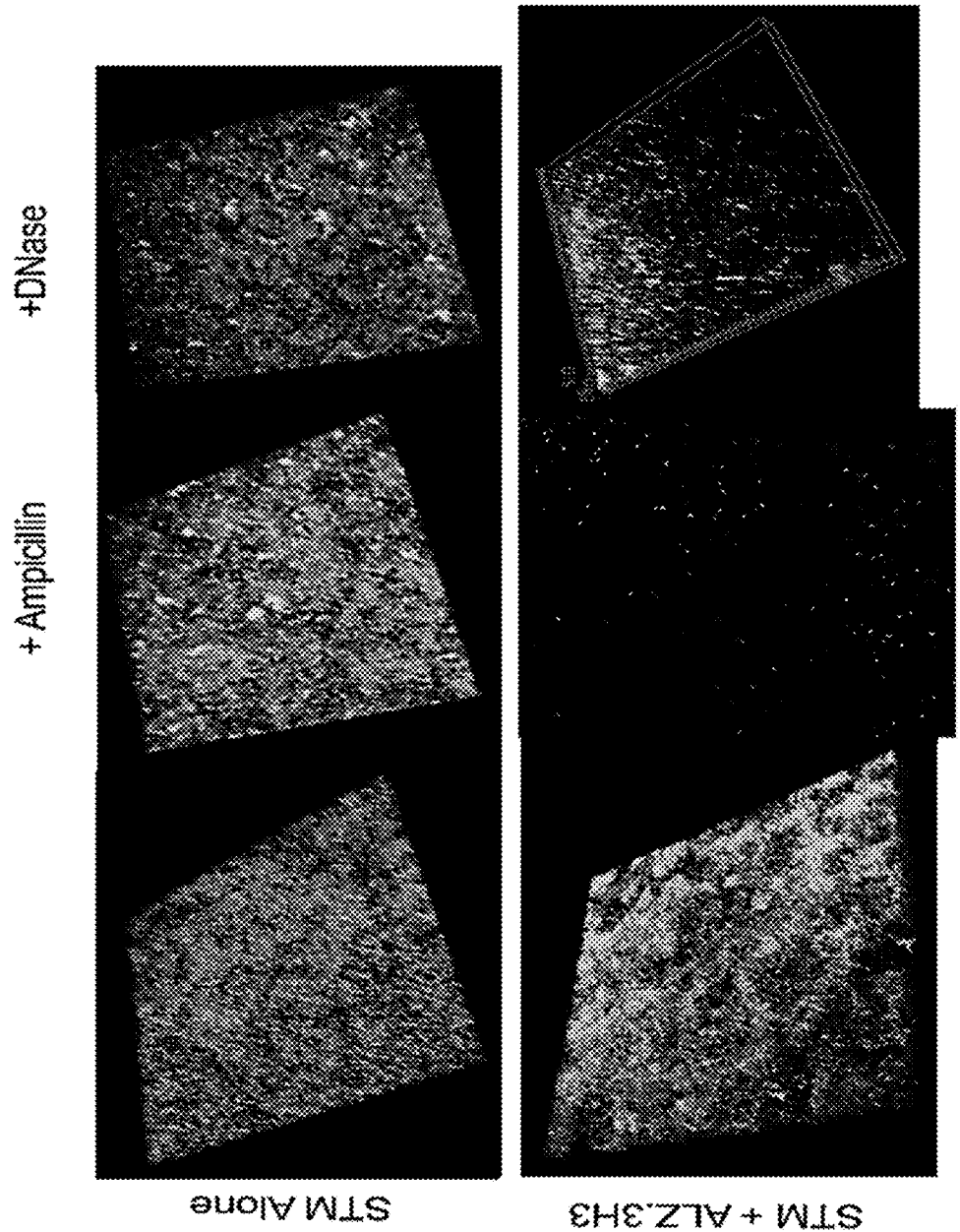
FIG. 7 depicts exemplary experimental results demonstrating synergism between ALZ.3H3 and antibiotic treatment reduces *S. Typhimurium* biofilm formation in vitro.

Typhimurium were established in the presence or absence of 0.5 mg/ml ALZ.3H3, after which biofilms were exposed to ampicillin for an additional 24 hours. As DNase is an additional integral component of *S. Typhimurium* biofilms, wildtype or ALZ.3H3 incubated biofilms were exposed to X DNase treatment for an additional 24 hours. Biofilms were then stained with Syto9 and visualized using CSML. Excessive washing steps were avoided in aims to examine the architecture of the biofilms. As antibiotic treatments are relatively ineffective against biofilm grown, no alteration in overall biofilm appearance was observed when wildtype biofilms were treated with ampicillin or DNase following biofilm establishment. However, when *S. Typhimurium* biofilms were incubated in the presence of ALZ.3H3 and antibiotic treatment, there was a significant reduction in the biofilm mass to the levels below detection (FIG. 7).

Figure 8:
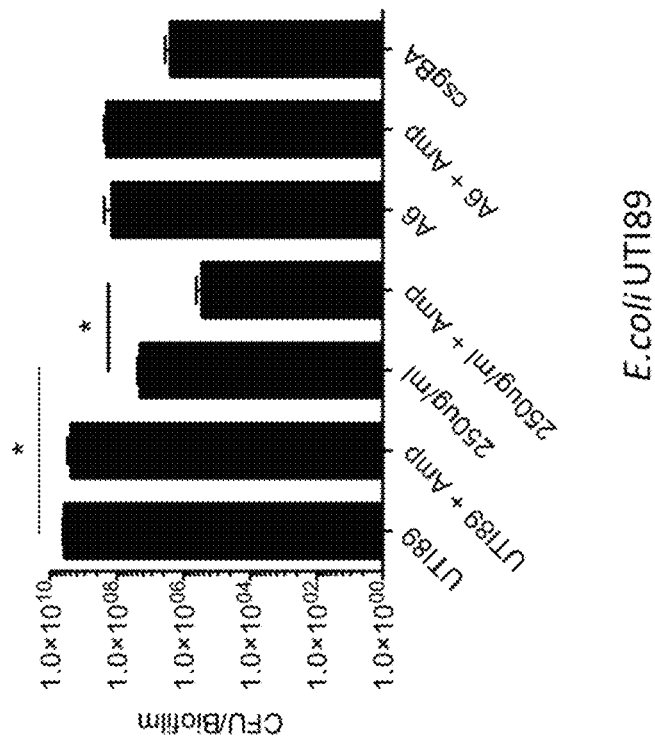
FIG. 8 depicts the colony forming units per biofilm grown with or without 3H3 and Ampicillin. Biofilms of *S. Typhimurium* (STM) or *E. coli* UTI89 grown in the absence or presence of 3H3 (250 ug/ml, 125 ug/ml, 50 ug/ml, 25 ug/ml, 10 ug/ml, 1 ug/ml) as well as grown with 0.5 mg/ml control A6 antibody on top of sterile glass coverslips for 72 hours at 26 C in a sterile 24 well dish. *S. Typhimurium* curli mutant (csgBA) and UTI89 curli mutant (csgBA) were also grown as a negative controls. In select conditions, biofilms were incubated for an additional 24 hours at 26 C with 30 ug/ml Ampicillin (Amp). The sterile glass coverslip, which was used as a surface for the biofilm to grow upon, was placed in a sterile 15 ml conical tube that contained 3 ml of sterile PBS. The biofilm was sonicated for 10 seconds at a setting of 4 using a ThermoFisher Sonic Dismembrator. Bacteria were enumerated by serial diluting 1:10 in sterile PBS and spot plating on agar plates.
Figure 8:
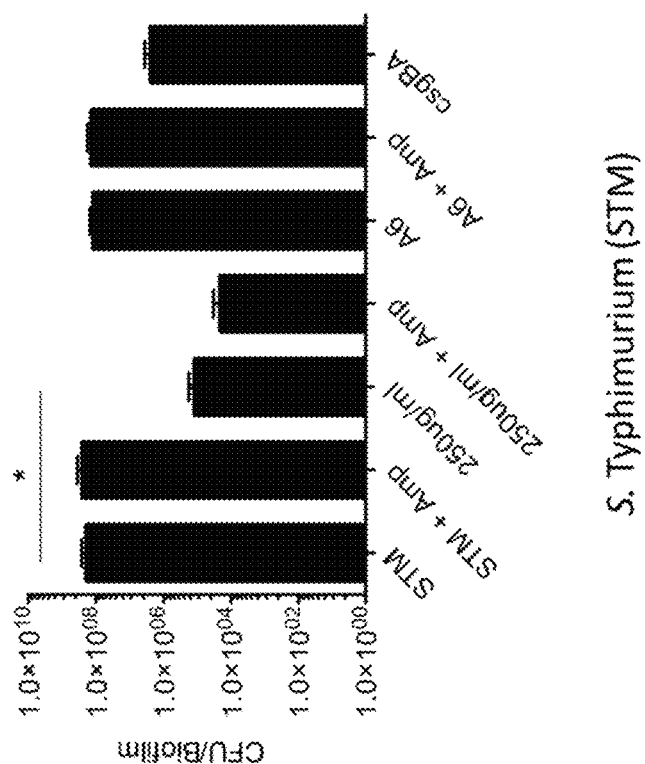

Biofilms of *S. Typhimurium* (STM) or *E. coli* UTI89 grown in the absence or presence of 3H3 (250 ug/ml, 125 ug/ml, 50 ug/ml, 25 ug/ml, 10 ug/ml, 1 ug/ml) as well as grown with 0.5 mg/ml control A6 antibody on top of sterile glass coverslips for 72 hours at 26 C in a sterile 24 well dish. *S. Typhimurium* curli mutant (csgBA) and UTI89 curli mutant (csgBA) were also grown as a negative controls. In select conditions, biofilms were incubated for an additional 24 hours at 26 C with 30 ug/ml Ampicillin (Amp). To determine the number of colony forming units per biofilm (CFU/biofilm), the sterile glass coverslip which was used as a surface for the biofilm to grow upon, was placed in a sterile 15 ml conical tube that contained 3 ml of sterile PBS. The biofilm was sonicated for 10 seconds at a setting of 4 using a ThermoFisher Sonic Dismembrator. Previous experiments confirmed that sonication at the previously mentioned settings did not kill the bacteria. Bacteria were enumerated by serial diluting 1:10 in sterile PBS and spot plating on agar plates. A reduction of CFU/biofilm was observed when STM and UTI89 are grown with 3H3, and an additional reduction in CFU/biofilm was observed when Ampicillin was added for an additional 24 hours (although this reduction may be enhanced with longer Ampicillin exposure times) (FIG. 8).

Figure 9:
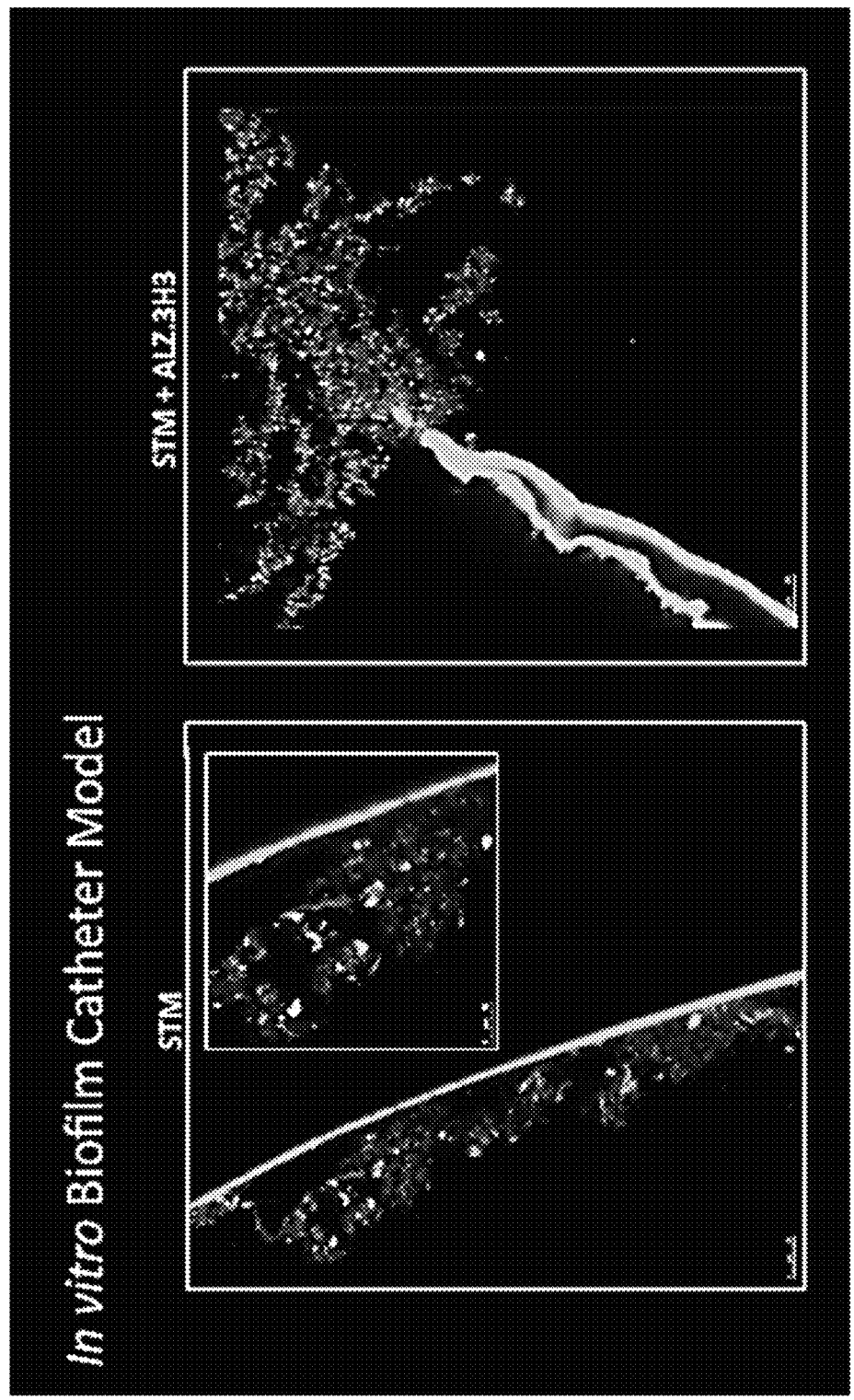
FIG. 9 depicts exemplary experimental results demonstrating that ALZ.3H3 treatment reduces *S. Typhimurium* biofilm formation in an in vitro catheter assay.
Figure 10:
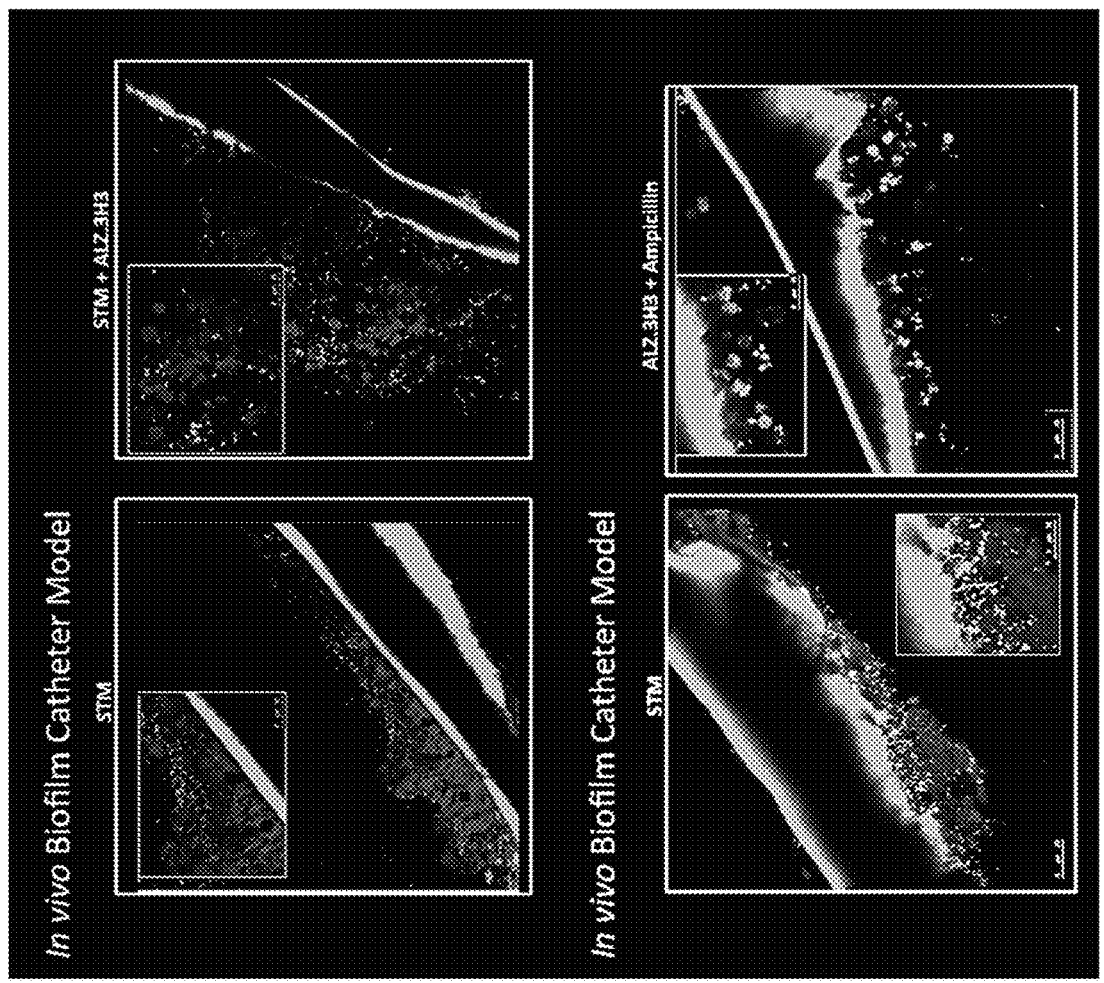
FIG. 10 depicts exemplary experimental results demonstrating that ALZ.3H3 treatment reduces *S. Typhimurium* biofilm formation in an in vivo catheter assay, and synergism between ALZ.3H3 and antibiotic treatment further reduces *S. Typhimurium* biofilm formation.

To investigate the ability of ALZ.3H3 to eliminate biofilm growth in a physiologically relevant model, biofilms of *S. Typhimurium* were grown on medical grade catheters in the presence or absence of ALZ.3H3 and the impact on catheter associated biofilm architecture was investigated. *Salmonella* biofilms were grown alone or in the presence of ALZ3H3 antibody upon sterile i.v. catheters. Bacteria were labeled green using GFP. Congo red was used to stain for curli amyloid fibrils. When grown in the presence of 0.5 mg/ml ALZ3H3 mAbs for 72 hours, the biofilm was dispersed. There was no significant staining with Congo red suggesting the lack of curli fibers on the biofilm (FIG. 9). To investigate the combination effect of ALZ3H3 and ampicillin on biofilm growth, mice were given 1 mg/ml Ampicillin in the drinking water 24 hours prior to catheter insertion. Sterile i.v. catheters were incubated for 24 hours with *Salmonella typhimurium* prior to insertion into the back flanks of Balb/C mice. 24 and 28 hours after catheter insertion 100 ug of ALZ3H3 was percutaneously inserted into the lumen of the catheter. 72 hours after catheter insertion, mice were euthanized and the catheters were removed. Bacteria were labeled green using GFP. Congo red was used to stain for curli amyloid fibrils. Catheters autofluoresced green. Untreated *Salmonella typhimurium* biofilms adhered closely to the catheter wall with curli throughout the biomass whereas biofilms treated with ALZ3H3 had a disperse morphology with little curli. Combination treatment with ALZ3H3 and ampicillin markedly reduced the biofilm growth on the catheter which displayed little to no amyloid incorporation (FIG. 10).

Figure 11:
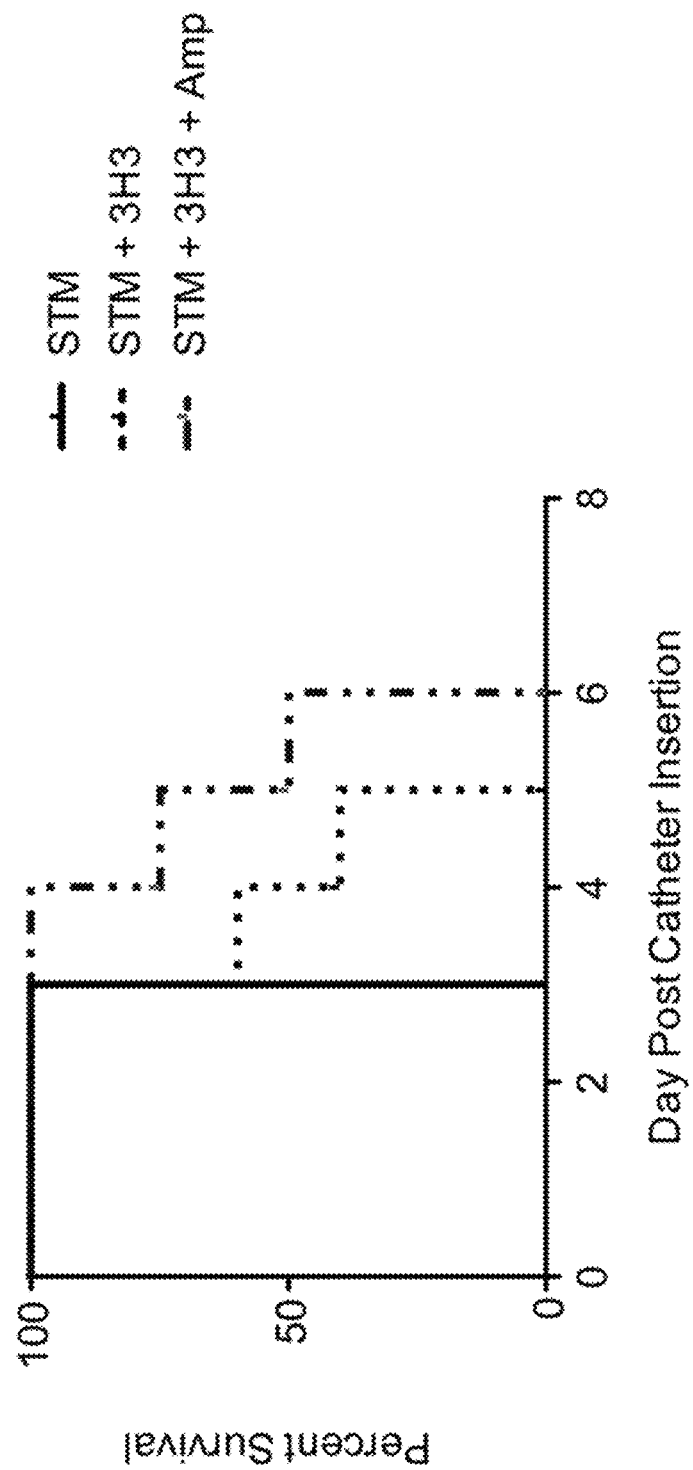
FIG. 11 depicts the percent survival of mice upon *S. Typhimurium* catheter insertion with ALZ.3H3 and Ampicillin treatment.

Catheters were colonized with biofilms of *S. Typhimurium* (STM) and one colonized catheter was inserted into each of 15 C67BL/6 mice (Cohorts: 5 mice that received STM catheters only, 5 mice that received STM catheters and percutaneous injections of 100 ug 3H3 and 5 mice that received STM catheters, percutaneous injections of 100 ug 3H3, and 1 mg/ml ampicillin (Amp) ad libitum in the drinking water. (**Ampicillin was added to drinking water 24 hours prior to catheter insertion). Beginning 24 hours after catheter insertion, in appropriate groups 100 ug/ml of 3H3 was inserted percutaneously into the lumen of the catheters every 24 hours post catheter insertion. Mice were monitored daily for survival (FIG. 11).

Example 2

Development of Pan-Amyloid Antibodies

Bacteria form multicellular communities termed biofilms in the nature and during infections to protect themselves against insults including antimicrobials and immune system. The extracellular matrix (ECM) of a biofilm is composed of polysaccharides, DNA, and proteins, including amyloids. Amyloids are naturally occurring, insoluble fibrillary proteins defined by a cross-beta sheet secondary structure. Congo Red is a specific dye that binds to amyloids and can be used to identify the bacterial amyloids. Bacteria uses utilize these proteins to decorate their biofilms. One of the best-studied bacterial amyloids is curli, specifically produced by Enterobacteriaceae. A human monoclonal antibody (mAb) that exhibits pan-amyloid binding activity inhibits formation of biofilms of both *E. coli* and *Salmonella typhimurium* in vitro and in vivo.

Figure 12:
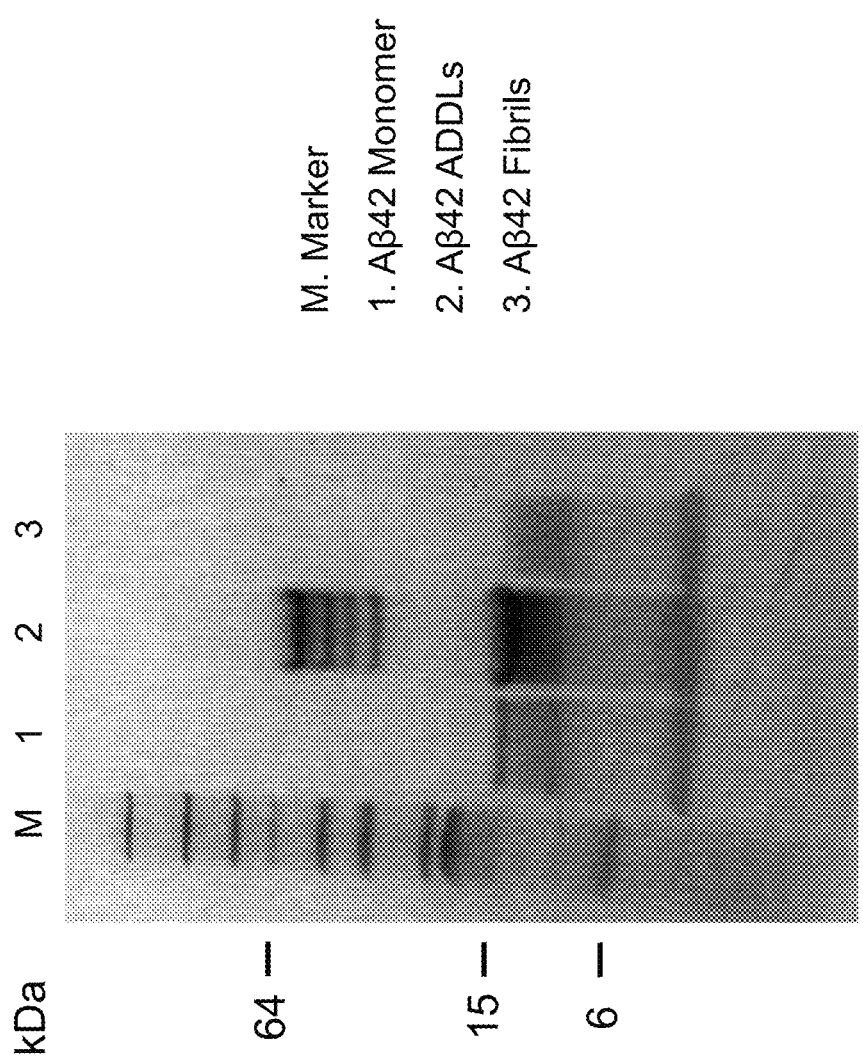
FIG. 12 depicts a coomassie stained SDS:PAGE gel of amyloid beta derived diffusible ligands (ADDLs), also known as globulomers, produced from Aβ42.
Figure 13:
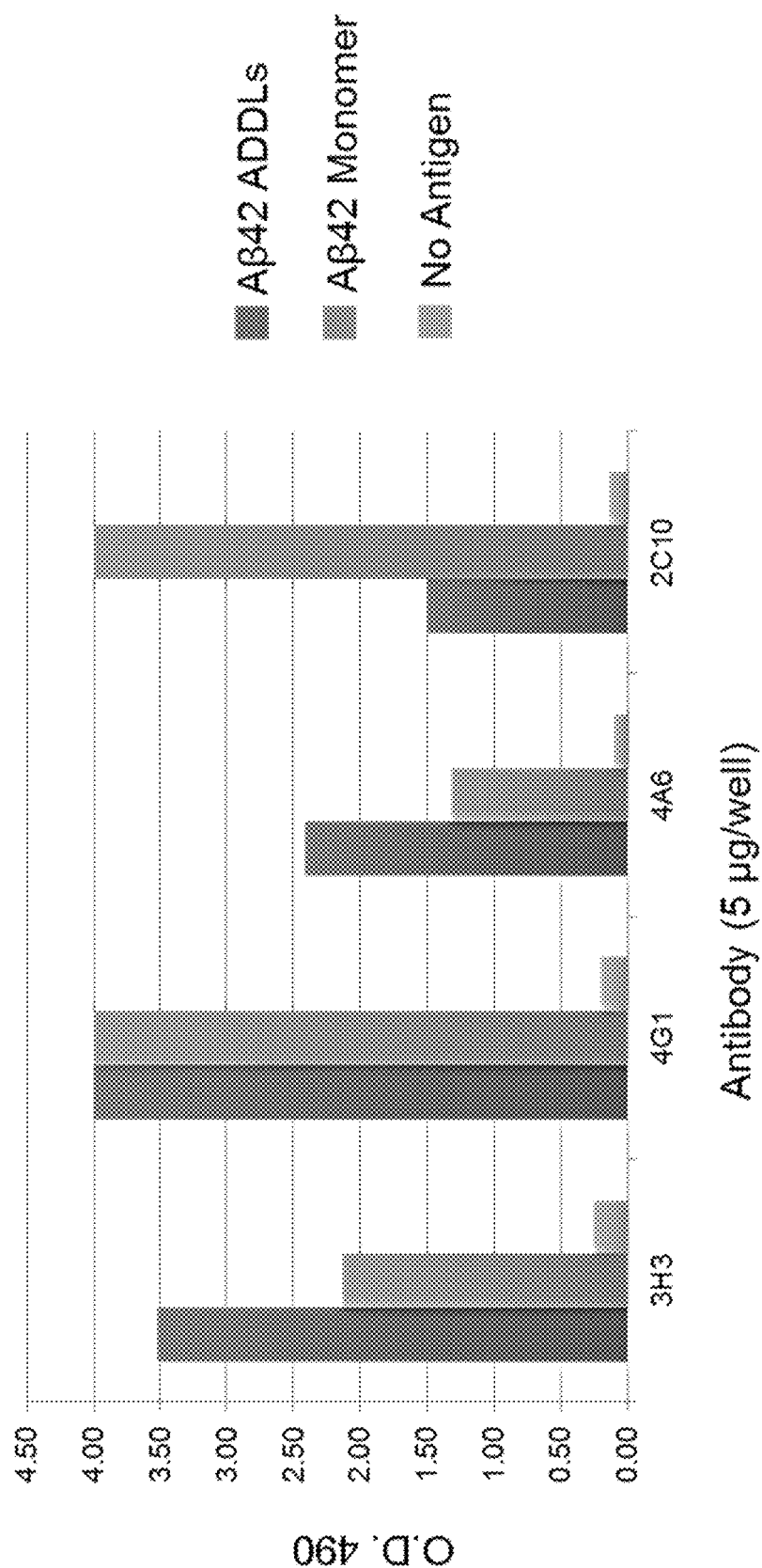
FIG. 13 depicts the binding of anti-amyloid antibodies to Aβ42 ADDLs and Aβ42 monomers, assessed by ELISA.

Amyloid beta derived diffusible ligands (ADDLs), also known as globulomers, produced from Aβ42 (FIG. 12). These ADDLs were used to screen for human mAbs that bind amyloid-specific epitopes. Hybridomas were created from B cells of a patient with a clinical diagnosis of mild-moderate Alzheimer's Disease, and three newly cloned mAbs (4G1, 4A6, and 2C10) were compared to ALZ.3H3 (FIG. 13). Monomeric Aβ42 adherent to an ELISA plate can adopt a conformation recognized by mAbs specific for conformational amyloid epitopes (Levites et al., 2015, J Neurosci, 35(16): 6265-6276).

MAb binding to Aβ42 conformers was measured by surface plasma resonance (SPR) (Table 1). Calculated affinity constants ($K_D$) were obtained using Qdat software. Compared to the the N-terminal biotinylated monomer, all of the mAbs exhibit lower affinity binding to some or all of the Aβ42 oligomers or fibrils. The 3H3 binding data is qualitatively most similar to the 4G1 and 6E10 mAbs. 4A6 and 2C10 preferentially bind Aβ fibrils.

TABLE 1

MAb binding to Aβ42 conformers. Oligomers (ADDLs/globulomers); CTB oligo (C-terminal biotinylated ADDLs/globulomers); CTB mono (C-terminal biotinylated monomers); NTB mono (N-terminal biotinylated monomers). 6E10 (mouse mAb to Aβ amino acids 1-16; BioLegend, San Diego, CA).

| Antibody | Oligomers nM | Fibrils nM | CTB oligo nM | CTB mono nM | NTB mono nM |
|---|---|---|---|---|---|
| 3H3 | 40 | 2.1 | 35 | 3.4 | 240 |
| 4G1 | 8.8 | 14 | 11.4 | 15 | 1700 |

TABLE 1-continued

MAb binding to Aβ42 conformers. Oligomers (ADDLs/globulomers);
CTB oligo (C-terminal biotinylated ADDLs/globulomers); CTB mono
(C-terminal biotinylated monomers); NTB mono (N-terminal
biotinylated monomers). 6E10 (mouse mAb to Aβ
amino acids 1-16; BioLegend, San Diego, CA).

| Antibody | Oligomers nM | Fibrils nM | CTB oligo nM | CTB mono nM | NTB mono nM |
|---|---|---|---|---|---|
| 4A6 | 1300 | 11 | >2000 | 16 | >2000 |
| 2C10 | >2000 | 16 | >2000 | >2000 | >2000 |
| 6E10 | 69 | 56 | 50 | 47 | 158 |

Figure 14:
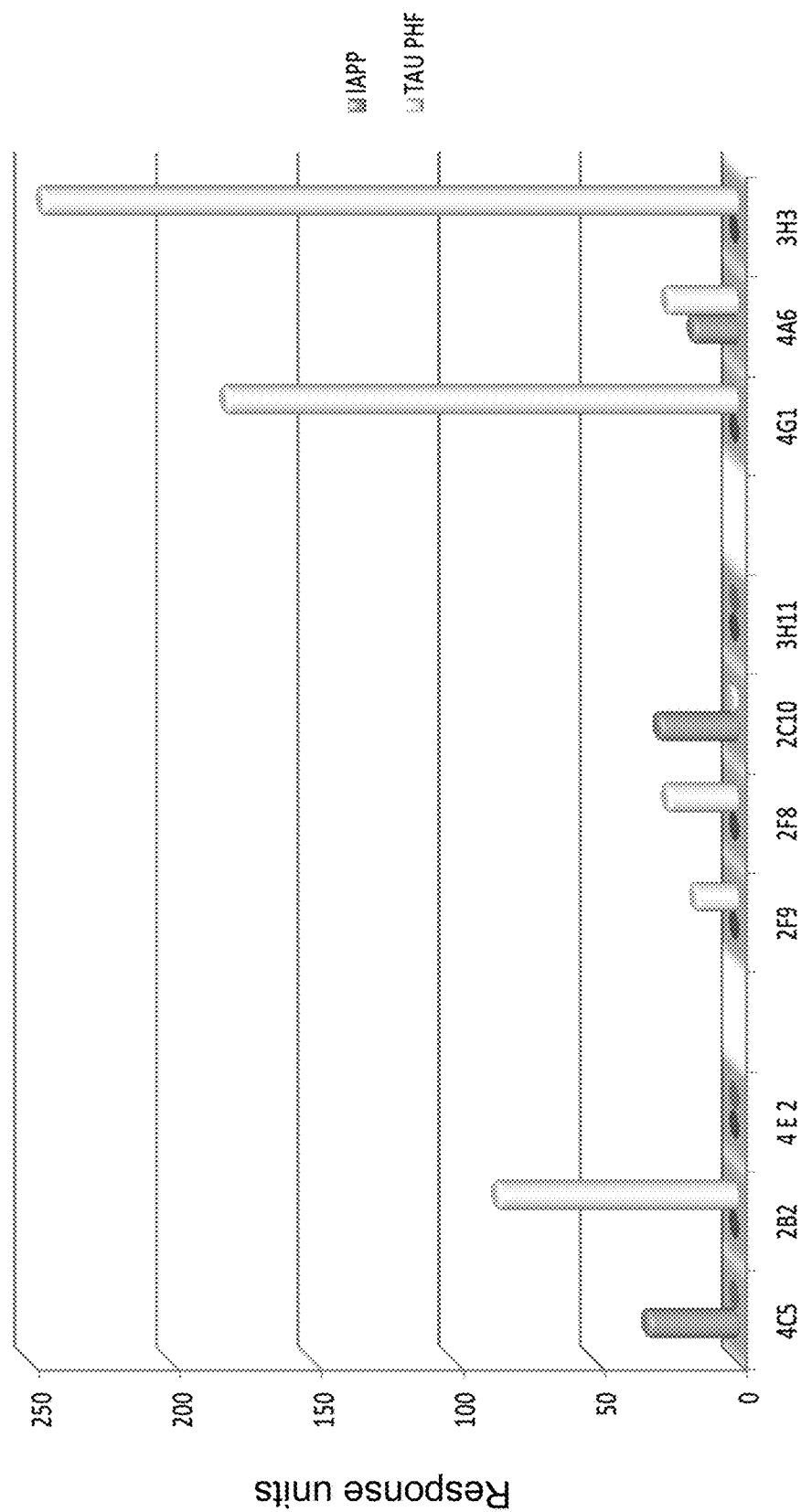
FIG. 14 depicts a surface plasma resonance (SPR) analysis for binding to aggregated islet amyloid peptide IAPP and tau paired helical filaments (TAU PHF) isolated from AD brain homogenates. The antibody concentrations used in this study were 110 nM for the IAPP and 66.7 nM for the Tau-PHF.

Human mAbs were assayed by SPR for binding to aggregated islet amyloid peptide IAPP and tau paired helical filaments (TAU PHF) isolated from AD brain homogenates (FIG. 14). The antibody concentrations used in this study were 110 nM for the IAPP and 66.7 nM for the Tau-PHF. The 3H3 and 4G1 mAbs are notable for binding to Tau PHF, consistent with recognition of a pan-amyloid epitope.

Figure 15:
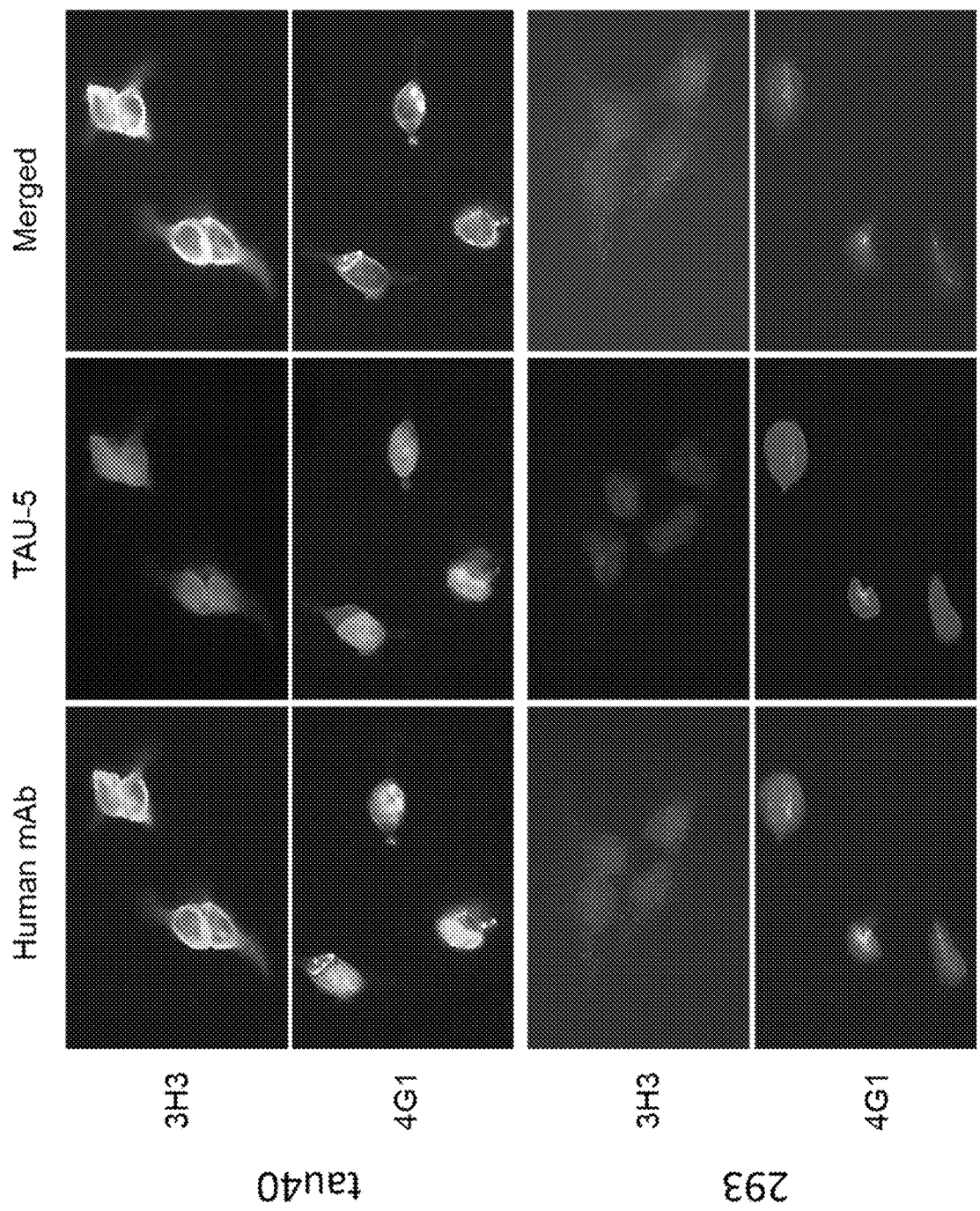
FIG. 15 depicts exemplary images of binding of the 4G1 and 3H3 mAbs to tau40 HEK-293 (tau40) and HEK-293 cell lines (293). Images are shown with human mAb only (left column), TAU-5 only (center column), or merged. 60×.

Binding of the 4G1 and 3H3 mAbs to tau40 HEK-293 and HEK-293 cell lines was assayed (FIG. 15).

Figure 16:
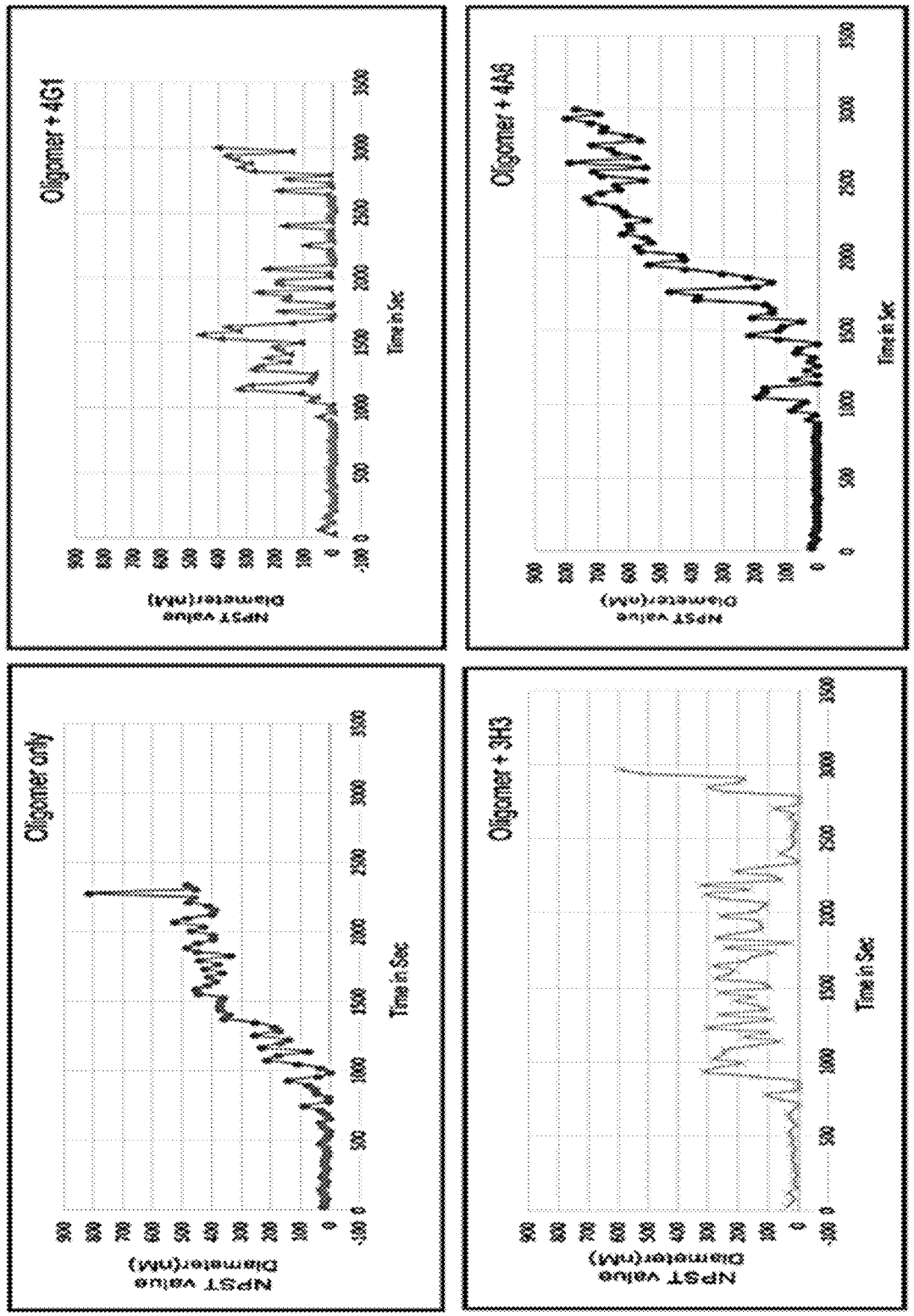
FIG. 16 depicts exemplary experimental results demonstrating the fibrillization of Aβ42 of amyloid beta oligomers alone or in presence of anti-amyloid mAbs, 3H3, 4G1 and 4A6.

Fibrillization of A1342 of amyloid beta oligomers alone or in presence of anti-amyloid mAbs, 3H3, 4G1 and 4A6 was assayed (FIG. 16).

Example 3

Use of Pan-Amyloid Antibodies as Therapeutic Antibodies Against *Y. pestis*

A member of Enterobacteriaceae family, *Yersinia pestis*, is the causative agent of the disease plague. *Y. pestis* infects primarily rodents, but which may also infect a wide array of other mammalian hosts, including humans. Fleas are employed by the pathogen as vectors, and the majority of transmission events are believed to occur through flea bites. Thus, the success of the bacterium depends, in part, on its ability to adapt and quickly respond to the disparate temperature environments encountered in the mammalian and flea hosts. *Y. pestis* form biofilms in the flea host and this trait has been associated with deadly infections in humans. Furthermore, biofilms of *Y. pestis* have also been observed in the granulomas produced during infection. However, the nature of these biofilms has yet to be explored.

A number of plasmid and chromosome-encoded virulence genes have been identified in *Y. pestis* including those involved in Congo red binding (Crb+ phenotype), which forms the basis of biofilm formation. However, these studies have not yet identified an amyloid protein which serves as the scaffold for *Y. pestis* biofilms.

Experiments are designed to identify and validate *Yersinia* amyloids that are involved in biofilm formation during infection using a proteomic approach and a software that has been established to identify amyloid proteins through sequence analysis. Candidate proteins are then selected and validated. Recombinant proteins are generated and tested for their amyloid activity using functional assays including Thioflavin T binding assay, Congo Red Spectrometry and Electron Microscopy.

After validation of amyloids, antibodies targeting these proteins will be generated. The mAbs generated are tested for their ability to disrupt biofilms, including biofilms of *Y. pseudotuberculosis, Y. enterocolitica* and *E. coli*, and for their in vitro anti-biofilm activity using standard biofilm assays. Antibodies that show a strong an anti-pan-amyloid activity are further tested in vivo against *Y. pseudotuberculosis, Y. enterocolitica* and *E. coli* using a catheter-biofilm model. mAbs that show the highest activity both in vitro and in vivo activities are potential therapeutic antibodies against *Y. pestis.*

Example 4

Antibody Sequences

```
SEQ ID NO: 1: ALZ.3H3 Heavy Chain (nucleotide)
SEQ ID NO: 2: ALZ.3H3 Heavy Chain (amino acid)
SEQ ID NO: 3: ALZ.3H3 Heavy Chain variable
region (nucleotide)
SEQ ID NO: 4: ALZ.3H3 Heavy Chain variable
region (amino acid)
SEQ ID NO: 5: ALZ.3H3 Heavy Chain (nucleotide) with
4nt before the Met
V-D-J-REGION: Nucleotides 62..448 of SEQ ID NO: 5
V-REGION Nucleotides 62..357 of SEQ ID NO: 5
FR1-IMGT (SEQ ID NO: 6; SEQ ID NO: 7)
CDR1-IMGT (SEQ ID NO: 8; SEQ ID NO: 9)
FR2-IMGT (SEQ ID NO: 10; SEQ ID NO: 11)
CDR2-IMGT (SEQ ID NO: 12; SEQ ID NO: 13)
FR3-IMGT (SEQ ID NO: 14; SEQ ID NO: 15)
CDR3-IMGT (SEQ ID NO: 16; SEQ ID NO: 17)
JUNCTION (SEQ ID NO: 18; SEQ ID NO: 19)
3'V-REGION (SEQ ID NO: 20; SEQ ID NO: 21)
N1-REGION (SEQ ID NO: 22; SEQ ID NO: 23)
D-REGION (SEQ ID NO: 24; SEQ ID NO: 25)
N2-REGION (SEQ ID NO: 26; SEQ ID NO: 27)
5'J-REGION (SEQ ID NO: 28; SEQ ID NO: 29)
J-REGION (SEQ ID NO: 30; SEQ ID NO: 31)
FR4-IMGT (SEQ ID NO: 32; SEQ ID NO: 33)
SEQ ID NO: 34: ALZ.3H3 Light Chain (nucleotide)
SEQ ID NO: 35: ALZ.3H3 Light Chain (amino acid)
V-J-REGION <Nucleotides 1..323 of SEQ ID NO: 34
V-REGION <Nucleotides 1..288 of SEQ ID NO: 34
FR1-IMGT (SEQ ID NO: 36; SEQ ID NO: 37)
CDR1-IMGT (SEQ ID NO: 38; SEQ ID NO: 39)
FR2-IMGT (SEQ ID NO: 40; SEQ ID NO: 41)
CDR2-IMGT (SEQ ID NO: 42; SEQ ID NO: 43)
FR3-IMGT (SEQ ID NO: 44; SEQ ID NO: 45)
CDR3-IMGT (SEQ ID NO: 46; SEQ ID NO: 47)
JUNCTION (SEQ ID NO: 48; SEQ ID NO: 49)
3'V-REGION (SEQ ID NO: 50; SEQ ID NO: 51)
N-REGION Nucleotides 289..290 of SEQ ID NO: 34
5'J-REGION Nucleotides 291..295 of SEQ ID NO: 34
J-REGION (SEQ ID NO: 52; SEQ ID NO: 53)
FR4-IMGT (SEQ ID NO: 54; SEQ ID NO: 55)
SEQ ID NO: 56 ALZ.4A6 Heavy Chain (nucleotide)
SEQ ID NO: 57 ALZ.4A6 Heavy Chain (amino acid)
SEQ ID NO: 58 ALZ.4A6 Light Chain (nucleotide)
SEQ ID NO: 59 ALZ.4A6 Light Chain (amino acid)
SEQ ID NO: 60 ALZ.4G1 Heavy Chain (nucleotide)
SEQ ID NO: 61 ALZ.4G1 Heavy Chain (amino acid)
SEQ ID NO: 62 ALZ.4G1 Light Chain (nucleotide)
SEQ ID NO: 63 ALZ.4G1 Light Chain (amino acid)
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody or antibody fragment thereof comprising a heavy chain CDR1 comprising the amino acid sequence of SEQ ID NO:9; a heavy chain CDR2 comprising amino acid sequence of SEQ ID NO:13; a heavy chain CDR3 comprising the amino acid sequence of SEQ ID NO:17; a light chain CDR1 comprising the amino acid sequence of SEQ ID NO: 39; a light chain CDR2 comprising the amino acid sequence of SEQ ID NO: 43; and a light chain CDR3 comprising the amino acid sequence of SEQ ID NO: 47.

2. The antibody or antibody fragment thereof of claim 1, encoded by a nucleic acid sequence comprising a nucleic acid sequence encoding a heavy chain CDR1, a heavy chain CDR2, and a heavy chain CDR3, wherein the heavy chain CDR1 is encoded by a nucleic acid sequence comprising the nucleic acid sequence of SEQ ID NO: 8; wherein the heavy chain CDR2 is encoded by a nucleic acid sequence comprising the nucleic acid sequence of SEQ ID NO: 12; and wherein the heavy chain CDR3 is encoded by a nucleic acid sequence comprising the nucleic acid sequence of SEQ ID NO:16.

3. The antibody or antibody fragment thereof of claim 1, encoded by a nucleic acid sequence encoding a light chain CDR1, a light chain CDR2, and a light chain CDR3, wherein the light chain CDR1 is encoded by a nucleic acid sequence comprising the nucleic acid sequence of SEQ ID NO:38; wherein the light chain CDR2 is encoded by a nucleic acid sequence comprising the nucleic acid sequence of SEQ ID NO: 42; and wherein the light chain CDR3 is encoded by a nucleic acid sequence comprising the nucleic acid sequence of SEQ ID NO:46.

4. The antibody of claim 1 wherein the antibody is in a format selected from the group consisting of scfv and Fv fragment.

5. An isolated polypeptide comprising the amino acid sequence SEQ ID NO:9, SEQ ID NO:13, SEQ ID NO:17, SEQ ID NO:39, SEQ ID NO: 43, and SEQ ID NO:47.

6. The isolated polypeptide of claim 5 wherein the polypeptide is in a format selected from the group consisting of scfv and Fv fragment.

7. An antibody or antibody fragment thereof comprising a heavy and light chain selected from the group consisting of:
   a) a heavy chain amino acid sequence comprising SEQ ID NO:2 and a light chain amino acid sequence comprising SEQ ID NO:35;
   b) a heavy chain amino acid sequence comprising SEQ ID NO:61 and a light chain amino acid sequence comprising SEQ ID NO:63; and
   c) a heavy chain amino acid sequence comprising SEQ ID NO:57 and a light chain amino acid sequence comprising SEQ ID NO:59.

8. The antibody or antibody fragment of claim 7, wherein the heavy and light chain is encoded by a nucleic acid sequence selected from the group consisting of:
   a) a heavy chain nucleic acid sequence comprising SEQ ID NO:1 and a light chain nucleic acid sequence comprising SEQ ID NO:34;
   b) a heavy chain nucleic acid sequence comprising SEQ ID NO:60 and a light chain nucleic acid sequence comprising SEQ ID NO:62; and
   c) a heavy chain nucleic acid sequence comprising SEQ ID NO:56 and a light chain nucleic acid sequence comprising SEQ ID NO:58.

9. An antibody or antibody fragment thereof comprising a heavy chain CDR1, wherein the heavy chain CDR1 comprises amino acid residues 23-35 of SEQ ID NO: 57; a heavy chain CDR2, wherein the heavy chain CDR2 comprises amino acid residues 50-59 of SEQ ID NO: 57; a heavy chain CDR3, wherein the heavy chain CDR3 comprises amino acid residues 97-116 of SEQ ID NO: 57; a light chain CDR1, wherein the light chain CDR1 comprises amino acid residues 24-34 of SEQ ID NO: 59; a light chain CDR2, wherein the light chain CDR2 comprises amino acid residues 49-56 of SEQ ID NO: 59; and a light chain CDR3, wherein the light chain CDR3 comprises amino acid residues 89-97 of SEQ ID NO: 59.

10. The antibody or antibody fragment thereof of claim 9, encoded by a nucleic acid sequence comprising a nucleic acid sequence encoding a heavy chain CDR1, a heavy chain CDR2, and a heavy chain CDR3, wherein the heavy chain CDR1 is encoded by a nucleic acid sequence comprising nucleotides 67-105 of SEQ ID NO: 56; wherein the heavy chain CDR2 is encoded by a nucleic acid sequence comprising nucleotides 148-177 of SEQ ID NO: 56; and wherein the heavy chain CDR3 is encoded by a nucleic acid sequence comprising nucleotides 289-348 of SEQ ID NO: 56.

11. The antibody or antibody fragment thereof of claim 9, encoded by a nucleic acid sequence comprising a nucleic acid sequence encoding a light chain CDR1, a light chain CDR2, and a light chain CDR3, wherein the light chain CDR1 is encoded by a nucleic acid sequence comprising nucleotides 70-102 of SEQ ID NO: 58; wherein the light chain CDR2 is encoded by a nucleic acid sequence comprising nucleotides 145-168 of SEQ ID NO: 58; and wherein the light chain CDR3 is encoded by a nucleic acid sequence comprising nucleotides 265-291 of SEQ ID NO: 58.

12. An antibody or antibody fragment thereof comprising a heavy chain CDR1, wherein the heavy chain CDR1 comprises amino acid residues 23-35 of SEQ ID NO: 61; a heavy chain CDR2, wherein the heavy chain CDR2 comprises amino acid residues 50-59 of SEQ ID NO: 61; a heavy chain CDR3, wherein the heavy chain CDR3 comprises amino acid residues 97-118 of SEQ ID NO: 61, a light chain CDR1, wherein the light chain CDR1 comprises amino acid residues 24-34 of SEQ ID NO: 63; a light chain CDR2, wherein the light chain CDR2 comprises amino acid residues 49-56 of SEQ ID NO: 63; and a light chain CDR3, wherein the light chain CDR3 comprises amino acid residues 89-97 of SEQ ID NO: 63.

13. The antibody or antibody fragment thereof of claim 12, encoded by a nucleic acid sequence comprising a nucleic acid sequence encoding a heavy chain CDR1, a heavy chain CDR2, and a heavy chain CDR3, wherein the heavy chain CDR1 is encoded by a nucleic acid sequence comprising nucleotides 67-105 of SEQ ID NO: 60; wherein the heavy chain CDR2 is encoded by a nucleic acid sequence comprising nucleotides 148-177 of SEQ ID NO: 60; and wherein the heavy chain CDR3 is encoded by a nucleic acid sequence comprising nucleotides 289-354 of SEQ ID NO: 60.

14. The antibody or antibody fragment thereof of claim 12, encoded by a nucleic acid sequence comprising a nucleic acid sequence encoding a light chain CDR1, a light chain CDR2, and a light chain CDR3, wherein the light chain CDR1 is encoded by a nucleic acid sequence comprising nucleotides 70-102 of SEQ ID NO: 62; wherein the light chain CDR2 is encoded by a nucleic acid sequence comprising nucleotides 145-168 of SEQ ID NO: 62; and wherein the light chain CDR3 is encoded by a nucleic acid sequence comprising nucleotides 265-291 of SEQ ID NO: 62.

* * * * *

SEQUENCE LISTING

<160> NUMBER OF SEQ ID NOS: 63

<210> SEQ ID NO 1
<211> LENGTH: 457
<212> TYPE: DNA
<213> ORGANISM: Artificial Sequence
<220> FEATURE:
<223> OTHER INFORMATION: Chemically Synthesized, ALZ.3H3 Heavy Chain

<400> SEQUENCE: 1

```
atggagtttg ggctgagctg ggtattcctc gttgctcttt taagaggtgt ccagtgtcaa      60
gtgcagctgg tggagtctgg gggaggcgtg gtccagcctg ggaggtccct gagactctcc     120
tgtgcagcct ctggattctc cttcagtacc tatggcatgc actgggtccg ccaggctcca     180
ggcaaggggc tggagtgggt ggcagttatt tcatatgatg gaagtaggaa atactatgca     240
gacaccggga aggccgatt caccatctcc agagacaact ccaagaacac gctgtatttg      300
gaaatgaacg gcctgagagc tgaagacacg gctgtgtatc actgtgcgaa agatcttaga     360
cgagaactcg gtttggcaa tcgggactat cactattatg gtatggacgc ctggggccaa     420
gggaccacgg tcaccgtctc ctcagcaagc accaagg                              457
```

<210> SEQ ID NO 2
<211> LENGTH: 152
<212> TYPE: PRT
<213> ORGANISM: Artificial Sequence
<220> FEATURE:
<223> OTHER INFORMATION: Chemically Synthesized, ALZ.3H3 Heavy Chain

<400> SEQUENCE: 2

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ser Phe
        35                  40                  45

Ser Thr Tyr Gly Met His Trp Val Arg Gln Ala Pro Gly Lys Gly Leu
    50                  55                  60

Glu Trp Val Ala Val Ile Ser Tyr Asp Gly Ser Arg Lys Tyr Tyr Ala
65                  70                  75                  80

Asp Thr Gly Lys Gly Arg Phe Thr Ile Ser Arg Asp Asn Ser Lys Asn
                85                  90                  95

Thr Leu Tyr Leu Glu Met Asn Gly Leu Arg Ala Glu Asp Thr Ala Val
            100                 105                 110

Tyr His Cys Ala Lys Asp Leu Arg Arg Glu Leu Gly Phe Gly Asn Arg
        115                 120                 125

Asp Tyr His Tyr Tyr Gly Met Asp Ala Trp Gly Gln Gly Thr Thr Val
    130                 135                 140

Thr Val Ser Ser Ala Ser Thr Lys
145                 150
```

<210> SEQ ID NO 3
<211> LENGTH: 400
<212> TYPE: DNA
<213> ORGANISM: Artificial Sequence
<220> FEATURE:
<223> OTHER INFORMATION: Chemically Synthesized, ALZ.3H3 Heavy Chain variable region

<400> SEQUENCE: 3

```
caagtgcagc tggtggagtc tgggggaggc gtggtccagc ctgggaggtc cctgagactc      60
tcctgtgcag cctctggatt ctccttcagt acctatggca tgcactgggt ccgccaggct     120
ccaggcaagg ggctggagtg ggtggcagtt atttcatatg atggaagtag gaaatactat     180
gcagacaccg ggaagggccg attcaccatc tccagagaca actccaagaa cacgctgtat     240
ttggaaatga acggcctgag agctgaagac acggctgtgt atcactgtgc gaaagatctt     300
agacgagaac tcgggtttgg caatcgggac tatcactatt atggtatgga cgcctggggc     360
caagggacca cggtcaccgt ctcctcagca agcaccaagg                           400
```

<210> SEQ ID NO 4
<211> LENGTH: 133
<212> TYPE: PRT
<213> ORGANISM: Artificial Sequence
<220> FEATURE:
<223> OTHER INFORMATION: Chemically Synthesized, ALZ.3H3 Heavy Chain
      variable region

<400> SEQUENCE: 4

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Arg Lys Tyr Tyr Ala Asp Thr Gly
    50                  55                  60

Lys Gly Arg Phe Thr Ile Ser Arg Asp Asn Ser Lys Asn Thr Leu Tyr
65                  70                  75                  80

Leu Glu Met Asn Gly Leu Arg Ala Glu Asp Thr Ala Val Tyr His Cys
                85                  90                  95

Ala Lys Asp Leu Arg Arg Glu Leu Gly Phe Gly Asn Arg Asp Tyr His
            100                 105                 110

Tyr Tyr Gly Met Asp Ala Trp Gly Gln Gly Thr Thr Val Thr Val Ser
        115                 120                 125

Ser Ala Ser Thr Lys
        130
```

<210> SEQ ID NO 5
<211> LENGTH: 461
<212> TYPE: DNA
<213> ORGANISM: Artificial Sequence
<220> FEATURE:
<223> OTHER INFORMATION: Chemically Synthesized, Heavy Chain
      (nucleotide) with 4nt before the Met

<400> SEQUENCE: 5

```
cgccatggag tttgggctga gctgggtatt cctcgttgct cttttaagag gtgtccagtg      60
tcaagtgcag ctggtggagt ctgggggagg cgtggtccag cctggagagt ccctgagact     120
ctcctgtgca gcctctggat tctccttcag tacctatggc atgcactggg tccgccaggc     180
tccaggcaag gggctggagt gggtggcagt tatttcatat gatggaagta ggaaatacta     240
tgcagacacc gggaagggcc gattcaccat ctccagagac aactccaaga acacgctgta     300
tttggaaatg aacggcctga gagctgaaga cacggctgtg tatcactgtg cgaaagatct     360
tagacgagaa ctcgggtttg gcaatcggga ctatcactat tatggtatgg acgcctgggg     420
ccaagggacc acggtcaccg tctcctcagc aagcaccaag g                         461
```

<210> SEQ ID NO 6
<211> LENGTH: 75
<212> TYPE: DNA
<213> ORGANISM: Artificial Sequence
<220> FEATURE:
<223> OTHER INFORMATION: Chemically Synthesized, FR1

<400> SEQUENCE: 6
caagtgcagc tggtggagtc tgggggaggc gtggtccagc ctgggaggtc cctgagactc      60
tcctgtgcag cctct                                                       75

<210> SEQ ID NO 7
<211> LENGTH: 25
<212> TYPE: PRT
<213> ORGANISM: Artificial Sequence
<220> FEATURE:
<223> OTHER INFORMATION: Chemically Synthesized, FR1

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 8
<211> LENGTH: 24
<212> TYPE: DNA
<213> ORGANISM: Artificial Sequence
<220> FEATURE:
<223> OTHER INFORMATION: Chemically Synthesized, CDR1

<400> SEQUENCE: 8
ggattctcct tcagtaccta tggc                                             24

<210> SEQ ID NO 9
<211> LENGTH: 8
<212> TYPE: PRT
<213> ORGANISM: Artificial Sequence
<220> FEATURE:
<223> OTHER INFORMATION: Chemically Synthesized, CDR1

<400> SEQUENCE: 9

Gly Phe Ser Phe Ser Thr Tyr Gly
1               5

<210> SEQ ID NO 10
<211> LENGTH: 51
<212> TYPE: DNA
<213> ORGANISM: Artificial Sequence
<220> FEATURE:
<223> OTHER INFORMATION: Chemically Synthesized, FR2

<400> SEQUENCE: 10
atgcactggg tccgccaggc tccaggcaag gggctggagt gggtggcagt t                51

<210> SEQ ID NO 11
<211> LENGTH: 17
<212> TYPE: PRT
<213> ORGANISM: Artificial Sequence
<220> FEATURE:
<223> OTHER INFORMATION: Chemically Synthesized, FR2

<400> SEQUENCE: 11

Met His Trp Val Arg Gln Ala Pro Gly Lys Gly Leu Glu Trp Val Ala
1               5                   10                  15

Val

<210> SEQ ID NO 12
<211> LENGTH: 24
<212> TYPE: DNA
<213> ORGANISM: Artificial Sequence
<220> FEATURE:
<223> OTHER INFORMATION: Chemically Synthesized, CDR2

<400> SEQUENCE: 12
atttcatatg atggaagtag gaaa        24

<210> SEQ ID NO 13
<211> LENGTH: 8
<212> TYPE: PRT
<213> ORGANISM: Artificial Sequence
<220> FEATURE:
<223> OTHER INFORMATION: Chemically Synthesized, CDR2

<400> SEQUENCE: 13

Ile Ser Tyr Asp Gly Ser Arg Lys
1               5

<210> SEQ ID NO 14
<211> LENGTH: 114
<212> TYPE: DNA
<213> ORGANISM: Artificial Sequence
<220> FEATURE:
<223> OTHER INFORMATION: Chemically Synthesized, FR3

<400> SEQUENCE: 14
tactatgcag acaccgggaa gggccgattc accatctcca gagacaactc caagaacacg        60
ctgtatttgg aaatgaacgg cctgagagct gaagacacgg ctgtgtatca ctgt        114

<210> SEQ ID NO 15
<211> LENGTH: 38
<212> TYPE: PRT
<213> ORGANISM: Artificial Sequence
<220> FEATURE:
<223> OTHER INFORMATION: Chemically Synthesized, FR3

<400> SEQUENCE: 15

Tyr Tyr Ala Asp Thr Gly Lys Gly Arg Phe Thr Ile Ser Arg Asp Asn
1               5                   10                  15

Ser Lys Asn Thr Leu Tyr Leu Glu Met Asn Gly Leu Arg Ala Glu Asp
            20                  25                  30

Thr Ala Val Tyr His Cys
        35

<210> SEQ ID NO 16
<211> LENGTH: 66
<212> TYPE: DNA
<213> ORGANISM: Artificial Sequence
<220> FEATURE:
<223> OTHER INFORMATION: Chemically Synthesized, CDR3

<400> SEQUENCE: 16
gcgaaagatc ttagacgaga actcgggttt ggcaatcggg actatcacta ttatggtatg        60
gacgcc        66

<210> SEQ ID NO 17
<211> LENGTH: 22
<212> TYPE: PRT

```
<213> ORGANISM: Artificial Sequence
<220> FEATURE:
<223> OTHER INFORMATION: Chemically Synthesized, CDR3

<400> SEQUENCE: 17

Ala Lys Asp Leu Arg Arg Glu Leu Gly Phe Gly Asn Arg Asp Tyr His
1               5                   10                  15

Tyr Tyr Gly Met Asp Ala
            20

<210> SEQ ID NO 18
<211> LENGTH: 72
<212> TYPE: DNA
<213> ORGANISM: Artificial Sequence
<220> FEATURE:
<223> OTHER INFORMATION: Chemically Synthesized, JUNCTION

<400> SEQUENCE: 18
tgtgcgaaag atcttagacg agaactcggg tttggcaatc gggactatca ctattatggt    60
atggacgcct gg                                                        72

<210> SEQ ID NO 19
<211> LENGTH: 24
<212> TYPE: PRT
<213> ORGANISM: Artificial Sequence
<220> FEATURE:
<223> OTHER INFORMATION: Chemically Synthesized, JUNCTION

<400> SEQUENCE: 19

Cys Ala Lys Asp Leu Arg Arg Glu Leu Gly Phe Gly Asn Arg Asp Tyr
1               5                   10                  15

His Tyr Tyr Gly Met Asp Ala Trp
            20

<210> SEQ ID NO 20
<211> LENGTH: 11
<212> TYPE: DNA
<213> ORGANISM: Artificial Sequence
<220> FEATURE:
<223> OTHER INFORMATION: Chemically Synthesized, 3'V-REGION

<400> SEQUENCE: 20
tgtgcgaaag a                                                         11

<210> SEQ ID NO 21
<211> LENGTH: 3
<212> TYPE: PRT
<213> ORGANISM: Artificial Sequence
<220> FEATURE:
<223> OTHER INFORMATION: Chemically Synthesized, 3'V-REGION

<400> SEQUENCE: 21

Cys Ala Lys
1

<210> SEQ ID NO 22
<211> LENGTH: 12
<212> TYPE: DNA
<213> ORGANISM: Artificial Sequence
<220> FEATURE:
<223> OTHER INFORMATION: Chemically Synthesized, N1-REGION

<400> SEQUENCE: 22
tcttagacga ga                                                        12
```

```
<210> SEQ ID NO 23
<211> LENGTH: 3
<212> TYPE: PRT
<213> ORGANISM: Artificial Sequence
<220> FEATURE:
<223> OTHER INFORMATION: Chemically Synthesized, N1-REGION

<400> SEQUENCE: 23

Leu Arg Arg
1

<210> SEQ ID NO 24
<211> LENGTH: 12
<212> TYPE: DNA
<213> ORGANISM: Artificial Sequence
<220> FEATURE:
<223> OTHER INFORMATION: Chemically Synthesized, D-REGION

<400> SEQUENCE: 24
actcgggttt gg                                                          12

<210> SEQ ID NO 25
<211> LENGTH: 3
<212> TYPE: PRT
<213> ORGANISM: Artificial Sequence
<220> FEATURE:
<223> OTHER INFORMATION: Chemically Synthesized, D-REGION

<400> SEQUENCE: 25

Leu Gly Phe
1

<210> SEQ ID NO 26
<211> LENGTH: 19
<212> TYPE: DNA
<213> ORGANISM: Artificial Sequence
<220> FEATURE:
<223> OTHER INFORMATION: Chemically Synthesized, N2-REGION

<400> SEQUENCE: 26
caatcgggac tatcactat                                                   19

<210> SEQ ID NO 27
<211> LENGTH: 6
<212> TYPE: DNA
<213> ORGANISM: Artificial Sequence
<220> FEATURE:
<223> OTHER INFORMATION: Chemically Synthesized, N2-REGION
<220> FEATURE:
<221> NAME/KEY: misc_feature
<222> LOCATION: (1)..(1)
<223> OTHER INFORMATION: n is a, c, g, or t

<400> SEQUENCE: 27 nrdyhy                                                                  6

<210> SEQ ID NO 28
<211> LENGTH: 18
<212> TYPE: DNA
<213> ORGANISM: Artificial Sequence
<220> FEATURE:
<223> OTHER INFORMATION: Chemically Synthesized, 5'J-REGION

<400> SEQUENCE: 28
tatggtatgg acgcctgg                                                    18
```

```
<210> SEQ ID NO 29
<211> LENGTH: 6
<212> TYPE: PRT
<213> ORGANISM: Artificial Sequence
<220> FEATURE:
<223> OTHER INFORMATION: Chemically Synthesized, 5'J-REGION

<400> SEQUENCE: 29

Tyr Gly Met Asp Ala Trp
1               5

<210> SEQ ID NO 30
<211> LENGTH: 48
<212> TYPE: DNA
<213> ORGANISM: Artificial Sequence
<220> FEATURE:
<223> OTHER INFORMATION: Chemically Synthesized, J-REGION

<400> SEQUENCE: 30
tatggtatgg acgcctgggg ccaagggacc acggtcaccg tctcctca                48

<210> SEQ ID NO 31
<211> LENGTH: 16
<212> TYPE: PRT
<213> ORGANISM: Artificial Sequence
<220> FEATURE:
<223> OTHER INFORMATION: Chemically Synthesized, J-REGION

<400> SEQUENCE: 31

Tyr Gly Met Asp Ala Trp Gly Gln Gly Thr Thr Val Thr Val Ser Ser
1               5                   10                  15

<210> SEQ ID NO 32
<211> LENGTH: 33
<212> TYPE: DNA
<213> ORGANISM: Artificial Sequence
<220> FEATURE:
<223> OTHER INFORMATION: Chemically Synthesized, FR4

<400> SEQUENCE: 32
tggggccaag ggaccacggt caccgtctcc tca                                33

<210> SEQ ID NO 33
<211> LENGTH: 11
<212> TYPE: PRT
<213> ORGANISM: Artificial Sequence
<220> FEATURE:
<223> OTHER INFORMATION: Chemically Synthesized, FR4

<400> SEQUENCE: 33

Trp Gly Gln Gly Thr Thr Val Thr Val Ser Ser
1               5                   10

<210> SEQ ID NO 34
<211> LENGTH: 591
<212> TYPE: DNA
<213> ORGANISM: Artificial Sequence
<220> FEATURE:
<223> OTHER INFORMATION: Chemically Synthesized, ALZ.3H3 Light Chain

<400> SEQUENCE: 34
gctgactcag cctcgctcag tgtccgggtc tcctggacag tcagtaacca tgtcctgcac    60
tggaaccaac agtgatattg gtggttataa ttatgtctcc tggtaccaac aacacccagg   120
caaagccccc aaactcatga tttatgatgt ctataagcgg ccctcagggg tccctgatcg   180
cttctctggc tccaagtctg gcaacacggc ctccctgacc atctctgggc tccaggctga   240
```

```
ggatgaggct gattactact gctgctcata tgcaggcacc aacaatttga tattcggcgg    300
agggaccaag ctgaccgtcc taggtcagcc caaggctgcc ccctcggtca ctctgttccc    360
gccctcctct gaggagcttc aagccaacaa ggccacactg gtgtgtctca taagtgactt    420
ctacccggga gccgtgacag tggcctggaa ggcagatagc agccccgtca aggcgggagt    480
ggagaccacc acaccctcca acaaagcaa caacaagtac gcggccagca gctatctgag     540
cctgacgcct gagcagtgga agtcccacag aagctacagc tgccaggtca c             591
```

<210> SEQ ID NO 35
<211> LENGTH: 196
<212> TYPE: PRT
<213> ORGANISM: Artificial Sequence
<220> FEATURE:
<223> OTHER INFORMATION: Chemically Synthesized, ALZ.3H3 Light Chain

<400> SEQUENCE: 35

```
Leu Thr Gln Pro Arg Ser Val Ser Gly Ser Pro Gly Gln Ser Val Thr
1               5                   10                  15

Met Ser Cys Thr Gly Thr Asn Ser Asp Ile Gly Gly Tyr Asn Tyr Val
            20                  25                  30

Ser Trp Tyr Gln Gln His Pro Gly Lys Ala Pro Lys Leu Met Ile Tyr
        35                  40                  45

Asp Val Tyr Lys Arg Pro Ser Gly Val Pro Asp Arg Phe Ser Gly Ser
    50                  55                  60

Lys Ser Gly Asn Thr Ala Ser Leu Thr Ile Ser Gly Leu Gln Ala Glu
65                  70                  75                  80

Asp Glu Ala Asp Tyr Tyr Cys Cys Ser Tyr Ala Gly Thr Asn Asn Leu
                85                  90                  95

Ile Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val
        195
```

<210> SEQ ID NO 36
<211> LENGTH: 67
<212> TYPE: DNA
<213> ORGANISM: Artificial Sequence
<220> FEATURE:
<223> OTHER INFORMATION: Chemically Synthesized, FR1

<400> SEQUENCE: 36

```
gctgactcag cctcgctcag tgtccgggtc tcctggacag tcagtaacca tgtcctgcac    60
tggaacc                                                              67
```

<210> SEQ ID NO 37
<211> LENGTH: 22

```
<212> TYPE: PRT
<213> ORGANISM: Artificial Sequence
<220> FEATURE:
<223> OTHER INFORMATION: Chemically Synthesized, FR1

<400> SEQUENCE: 37

Ala Asp Ser Ala Ser Leu Ser Val Arg Val Ser Trp Thr Val Ser Asn
1               5                   10                  15

His Val Leu His Trp Asn
            20

<210> SEQ ID NO 38
<211> LENGTH: 27
<212> TYPE: DNA
<213> ORGANISM: Artificial Sequence
<220> FEATURE:
<223> OTHER INFORMATION: Chemically Synthesized, CDR1

<400> SEQUENCE: 38
aacagtgata ttggtggtta taattat                                      27

<210> SEQ ID NO 39
<211> LENGTH: 9
<212> TYPE: PRT
<213> ORGANISM: Artificial Sequence
<220> FEATURE:
<223> OTHER INFORMATION: Chemically Synthesized, CDR1

<400> SEQUENCE: 39

Asn Ser Asp Ile Gly Gly Tyr Asn Tyr
1               5

<210> SEQ ID NO 40
<211> LENGTH: 51
<212> TYPE: DNA
<213> ORGANISM: Artificial Sequence
<220> FEATURE:
<223> OTHER INFORMATION: Chemically Synthesized, FR2

<400> SEQUENCE: 40
gtctcctggt accaacaaca cccaggcaaa gcccccaaac tcatgattta t            51

<210> SEQ ID NO 41
<211> LENGTH: 17
<212> TYPE: PRT
<213> ORGANISM: Artificial Sequence
<220> FEATURE:
<223> OTHER INFORMATION: Chemically Synthesized, FR2

<400> SEQUENCE: 41

Val Ser Trp Tyr Gln Gln His Pro Gly Lys Ala Pro Lys Leu Met Ile
1               5                   10                  15

Tyr

<210> SEQ ID NO 42
<211> LENGTH: 9
<212> TYPE: DNA
<213> ORGANISM: Artificial Sequence
<220> FEATURE:
<223> OTHER INFORMATION: Chemically Synthesized, CDR2

<400> SEQUENCE: 42 gatgtctat                                                          9

<210> SEQ ID NO 43
```

```
<211> LENGTH: 3
<212> TYPE: PRT
<213> ORGANISM: Artificial Sequence
<220> FEATURE:
<223> OTHER INFORMATION: Chemically Synthesized, CDR2

<400> SEQUENCE: 43

Asp Val Tyr
1

<210> SEQ ID NO 44
<211> LENGTH: 108
<212> TYPE: DNA
<213> ORGANISM: Artificial Sequence
<220> FEATURE:
<223> OTHER INFORMATION: Chemically Synthesized, FR3

<400> SEQUENCE: 44
aagcggccct cagggtccc tgatcgcttc tctggctcca agtctggcaa cacggcctcc    60
ctgaccatct ctgggctcca ggctgaggat gaggctgatt actactgc              108

<210> SEQ ID NO 45
<211> LENGTH: 36
<212> TYPE: PRT
<213> ORGANISM: Artificial Sequence
<220> FEATURE:
<223> OTHER INFORMATION: Chemically Synthesized, FR3

<400> SEQUENCE: 45

Lys Arg Pro Ser Gly Val Pro Asp Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 46
<211> LENGTH: 30
<212> TYPE: DNA
<213> ORGANISM: Artificial Sequence
<220> FEATURE:
<223> OTHER INFORMATION: Chemically Synthesized, CDR3

<400> SEQUENCE: 46
tgctcatatg caggcaccaa caatttgata                                   30

<210> SEQ ID NO 47
<211> LENGTH: 10
<212> TYPE: PRT
<213> ORGANISM: Artificial Sequence
<220> FEATURE:
<223> OTHER INFORMATION: Chemically Synthesized, CDR3

<400> SEQUENCE: 47

Cys Ser Tyr Ala Gly Thr Asn Asn Leu Ile
1               5                   10

<210> SEQ ID NO 48
<211> LENGTH: 36
<212> TYPE: DNA
<213> ORGANISM: Artificial Sequence
<220> FEATURE:
<223> OTHER INFORMATION: Chemically Synthesized, JUNCTION

<400> SEQUENCE: 48
```
tgctgctcat atgcaggcac caacaatttg atattc                    36

<210> SEQ ID NO 49
<211> LENGTH: 12
<212> TYPE: PRT
<213> ORGANISM: Artificial Sequence
<220> FEATURE:
<223> OTHER INFORMATION: Chemically Synthesized, JUNCTION

<400> SEQUENCE: 49

Cys Cys Ser Tyr Ala Gly Thr Asn Asn Leu Ile Phe
1               5                   10

<210> SEQ ID NO 50
<211> LENGTH: 29
<212> TYPE: DNA
<213> ORGANISM: Artificial Sequence
<220> FEATURE:
<223> OTHER INFORMATION: Chemically Synthesized, 3'V-REGION

<400> SEQUENCE: 50
tgctgctcat atgcaggcac caacaattt                            29

<210> SEQ ID NO 51
<211> LENGTH: 9
<212> TYPE: PRT
<213> ORGANISM: Artificial Sequence
<220> FEATURE:
<223> OTHER INFORMATION: Chemically Synthesized, 3'V-REGION

<400> SEQUENCE: 51

Cys Cys Ser Tyr Ala Gly Thr Asn Asn
1               5

<210> SEQ ID NO 52
<211> LENGTH: 33
<212> TYPE: DNA
<213> ORGANISM: Artificial Sequence
<220> FEATURE:
<223> OTHER INFORMATION: Chemically Synthesized, J-REGION

<400> SEQUENCE: 52
tattcggcgg agggaccaag ctgaccgtcc tag                        33

<210> SEQ ID NO 53
<211> LENGTH: 10
<212> TYPE: PRT
<213> ORGANISM: Artificial Sequence
<220> FEATURE:
<223> OTHER INFORMATION: Chemically Synthesized, J-REGION

<400> SEQUENCE: 53

Phe Gly Gly Gly Thr Lys Leu Thr Val Leu
1               5                   10

<210> SEQ ID NO 54
<211> LENGTH: 31
<212> TYPE: DNA
<213> ORGANISM: Artificial Sequence
<220> FEATURE:
<223> OTHER INFORMATION: Chemically Synthesized, FR4

<400> SEQUENCE: 54
ttcggcggag ggaccaagct gaccgtccta g                         31

<210> SEQ ID NO 55

```
<211> LENGTH: 10
<212> TYPE: PRT
<213> ORGANISM: Artificial Sequence
<220> FEATURE:
<223> OTHER INFORMATION: Chemically Synthesized, FR4

<400> SEQUENCE: 55

Phe Gly Gly Gly Thr Lys Leu Thr Val Leu
1               5                   10

<210> SEQ ID NO 56
<211> LENGTH: 381
<212> TYPE: DNA
<213> ORGANISM: Artificial Sequence
<220> FEATURE:
<223> OTHER INFORMATION: Chemically Synthesized, ALZ.4A6 Heavy Chain

<400> SEQUENCE: 56
caggtccaac tggtgcaatc tggggctgaa gtgaagaagc tggggcctc aatgagagtc      60 tcctgcaagg cttctggtta cacctacacc gcctactata cattggat gcgacaggcc      120 cctggacaag ggcttgagtg gatgggatgg atcaacccc acattggctc acaaattat      180 gcggagaagt ttcgcggcag ggtcaccttg accagacaa cgtccatcaa gacagcctac      240
atggatctcg acaggctgac gtctgacgac acggccatat attactgtgc gagagtccga      300
gccccccgga gtataagtgg aactctcaac tcttacggaa tggacgtctg gggccaaggg      360
accacggtcg ccgtctcttc a                                               381

<210> SEQ ID NO 57
<211> LENGTH: 127
<212> TYPE: PRT
<213> ORGANISM: Artificial Sequence
<220> FEATURE:
<223> OTHER INFORMATION: Chemically Synthesized, ALZ.4A6 Heavy Chain

<400> SEQUENCE: 57

Gln Val Gln Leu Val Gln Ser Gly Ala Glu Val Lys Lys Pro Gly Ala
1               5                   10                  15

Ser Met Arg Val Ser Cys Lys Ala Ser Gly Tyr Thr Tyr Thr Ala Tyr
                20                  25                  30

Tyr Ile His Trp Met Arg Gln Ala Pro Gly Gln Gly Leu Glu Trp Met
            35                  40                  45

Gly Trp Ile Asn Pro His Ile Gly Ser Thr Asn Tyr Ala Glu Lys Phe
        50                  55                  60

Arg Gly Arg Val Thr Leu Thr Arg Asp Thr Ser Ile Lys Thr Ala Tyr
65                  70                  75                  80

Met Asp Leu Asp Arg Leu Thr Ser Asp Asp Thr Ala Ile Tyr Tyr Cys
                85                  90                  95

Ala Arg Val Arg Ala Pro Arg Ser Ile Ser Gly Thr Leu Asn Ser Tyr
                100                 105                 110

Gly Met Asp Val Trp Gly Gln Gly Thr Thr Val Ala Val Ser Ser
            115                 120                 125

<210> SEQ ID NO 58
<211> LENGTH: 321
<212> TYPE: DNA
<213> ORGANISM: Artificial Sequence
<220> FEATURE:
<223> OTHER INFORMATION: Chemically Synthesized, ALZ.4A6 Light Chain

<400> SEQUENCE: 58
```

```
gacatcgtga tgacccagtc tccttcgtcc ctgtctgcat ctgtgggaga cagggtcgtc      60
atcacttgcc gggcaagtct gagaattggc accttttta  attggtatca gcagacacaa    120
gggagagccc ccaaactcct ggtgtcttct gcgtccactt tgcaaagtgg cgtcccatca    180
aggttcagtg gcagtggatc tgggacggat tcactctca  ccattaacag tctgcaacct    240
gaagattttg caacttacta ctgtcaacag agttacagta ccacgtggac attcggccaa    300
gggaccaagg tggaactcaa a                                              321
```

<210> SEQ ID NO 59
<211> LENGTH: 107
<212> TYPE: PRT
<213> ORGANISM: Artificial Sequence
<220> FEATURE:
<223> OTHER INFORMATION: Chemically Synthesized, ALZ.4A6 Light Chain

<400> SEQUENCE: 59

```
Asp Ile Val Met Thr Gln Ser Pro Ser Ser Leu Ser Ala Ser Val Gly
1               5                   10                  15

Asp Arg Val Val Ile Thr Cys Arg Ala Ser Leu Arg Ile Gly Thr Phe
            20                  25                  30

Leu Asn Trp Tyr Gln Gln Thr Gln Gly Arg Ala Pro Lys Leu Leu Val
        35                  40                  45

Ser Ser Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Thr Thr Trp
                85                  90                  95

Thr Phe Gly Gln Gly Thr Lys Val Glu Leu Lys
            100                 105
```

<210> SEQ ID NO 60
<211> LENGTH: 387
<212> TYPE: DNA
<213> ORGANISM: Artificial Sequence
<220> FEATURE:
<223> OTHER INFORMATION: Chemically Synthesized, ALZ.4G1 Heavy Chain

<400> SEQUENCE: 60

```
gaggagcacc tggtggagtc tgggggagcc ttggtccagc ctggggggtc cctgagactc      60
tcctgtgaag cctctggatt cacctttcgt agttattgga tgacctgggt ccgccaggct    120
ccagggaagg ggctggaatg gctggccaac atcaaacaag atggaagtga ctattactat    180
gtcgactctg tgaagggccg attcaccatc tccagagaca acgccaagaa tacactatat    240
ctgcagatga caacctgag  agccgacgac acggccgttt attttttgtgc gagagatgcg    300 agatatcggg acactacctg gccgcaatac tatttttact acttcatgga cgtctggggc    360
aaggggacca cggtcaccgt ctcctca                                        387
```

<210> SEQ ID NO 61
<211> LENGTH: 129
<212> TYPE: PRT
<213> ORGANISM: Artificial Sequence
<220> FEATURE:
<223> OTHER INFORMATION: Chemically Synthesized, ALZ.4G1 Heavy Chain

<400> SEQUENCE: 61

```
Glu Glu His Leu Val Glu Ser Gly Gly Ala Leu Val Gln Pro Gly Gly
1               5                   10                  15
```

Ser Leu Arg Leu Ser Cys Glu Ala Ser Gly Phe Thr Phe Arg Ser Tyr
            20                  25                  30

Trp Met Thr Trp Val Arg Gln Ala Pro Gly Lys Gly Leu Glu Trp Leu
        35                  40                  45

Ala Asn Ile Lys Gln Asp Gly Ser Asp Tyr Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Arg Ala Asp Asp Thr Ala Val Tyr Phe Cys
                85                  90                  95

Ala Arg Asp Ala Arg Tyr Arg Asp Thr Thr Trp Pro Gln Tyr Tyr Phe
            100                 105                 110

Tyr Tyr Phe Met Asp Val Trp Gly Lys Gly Thr Thr Val Thr Val Ser
        115                 120                 125

Ser

<210> SEQ ID NO 62
<211> LENGTH: 321
<212> TYPE: DNA
<213> ORGANISM: Artificial Sequence
<220> FEATURE:
<223> OTHER INFORMATION: Chemically Synthesized, ALZ.4G1 Light Chain

<400> SEQUENCE: 62
gacatccagt tgacccagtc tccatcctcc ctgtctgcct ctataggcga cagagtcacc        60
gtcacttgcc gggccagtca gagcattagt aattatttaa attggtatca gcagaaacca      120
gggaaagccc ctaaactcct gatctatgct gcatccaatt tgcatactgg ggtcccatcg      180
aggttcagtg gcagtgggtc tgggacacat tttactctca ccatcagcag tctgcaacct      240
gaagattttg caacttacta ctgtcaactg agttacaata cccgagaac tttcggccct      300 gggaccacag tggatatcag a                                                321

<210> SEQ ID NO 63
<211> LENGTH: 107
<212> TYPE: PRT
<213> ORGANISM: Artificial Sequence
<220> FEATURE:
<223> OTHER INFORMATION: Chemically Synthesized, ALZ.4G1 Light Chain

<400> SEQUENCE: 63

Asp Ile Gln Leu Thr Gln Ser Pro Ser Ser Leu Ser Ala Ser Ile Gly
1               5                   10                  15

Asp Arg Val Thr Val Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu His Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Phe Ala Thr Tyr Tyr Cys Gln Leu Ser Tyr Asn Asn Pro Arg
                85                  90                  95

Thr Phe Gly Pro Gly Thr Thr Val Asp Ile Arg
            100                 105